(12) United States Patent
Clark

(10) Patent No.: US 7,258,864 B2
(45) Date of Patent: Aug. 21, 2007

(54) METHODS FOR TREATMENT OF INSULIN-LIKE GROWTH FACTOR-1 (IGF-1) DEFICIENCY

(75) Inventor: Ross G. Clark, Auckland (NZ)

(73) Assignee: Tercica, Inc., South San Francisco, CA (US)

( * ) Notice: Subject to any disclaimer, the term of this patent is extended or adjusted under 35 U.S.C. 154(b) by 351 days.

(21) Appl. No.: 10/939,111

(22) Filed: Sep. 9, 2004

(65) Prior Publication Data

US 2005/0059598 A1 Mar. 17, 2005

Related U.S. Application Data

(60) Provisional application No. 60/502,579, filed on Sep. 12, 2003.

(51) Int. Cl.
*C07K 14/65* (2006.01)
*A61K 38/00* (2006.01)
*A61K 38/30* (2006.01)

(52) U.S. Cl. ............... 424/198.1; 514/2; 514/12; 514/21; 530/303; 530/311; 530/399

(58) Field of Classification Search ............... None
See application file for complete search history.

(56) References Cited

U.S. PATENT DOCUMENTS 5,741,776 A * 4/1998 Clark et al. ............... 514/12
5,824,642 A * 10/1998 Attie et al. ............... 514/12

OTHER PUBLICATIONS

Clark, R., Recombinant human insulin-like growth factor 1 (IGF-1): risks and benefits of normalizing blood IGF-1 concentrations, 2004, Hormone Research, vol. 62, Supplement 1, pp. 93-100.*
Zvi Laron. Somatomedin-1 (Recombinant) Insulin-like Growth Factor-1—Clinical Pharmacology and Potential Treatment of Endocrine and Metabolic Disorders. BioDrugs 1999, Jan. 11 (1): 55-70.
Clemmons DR et al., "Factors controlling blood concentration of somatomedin C", 1984, Clin Endocrinol Metab 13:113-43.
Clemmons DR et al., "Evaluation of acromegaly by radioimmunoassay of somatomedin-c", 1979, N Engl J Med 301:1138-42.
Clemmons DR et al., "Somatomedin-C/insulin-like growth factor I in acromegaly", 1986, Olin Endocrinol Metal 15:629-51.
Juul, 2003, "Serum levels of insulin-like growth factor I and its binding proteins in health and disease", GH and IGF Research 13: 113-170.
Liu, J-L and LeRoith, D, "Insulin-like growth factor 1 is essential for postnatal growth in response to growth hormone", 1999, Endocrinology 140:5178-84.
Lupu, F et al., "Roles of growth hormone and insulin-like growth factor 1 in Mouse postnatal growth", 2001, Dev Biol 229:141-62.
Salmon WD Jr. et al., "The journal of laboratory and clinical medicine", 1957, J Lab Olin Med, 49:825-36.
Van Wyk JJ. The Somatomedins: biological actions and physiological control mechanisms in Hormonal Proteins and Peptides, ed CH Li, 12:81-175, Orlando, FL:Academic Press, this reference does not have a publication date.
Zhou, Y et al., A mammalian model for laron syndrome produced by targeted disruption of the mouse growth hormone receptor/binding protein gene (the Laron mouse) 1997, Proc Natl Acad Sci. USA 94:13215-20.
Azcona et al., (1999), "Growth Response to rhIGF-1 80 µg/kg twice daily in children with growth hormone insensitivity syndrome: relationship to severity of clinical phenotype", Clinical Endocrinology, 51, pp. 787-792.

* cited by examiner

*Primary Examiner*—Bridget Bunner
*Assistant Examiner*—Ian Dang
(74) *Attorney, Agent, or Firm*—Carol L. Francis; Paula A. Borden; Bozicevic, Field & Francis LLP

(57) ABSTRACT

The present invention provides methods and compositions for increasing the growth rates, alleviating the symptoms, or improving the metabolism of human patients having insulin-like growth factor-1 deficiency (IGFD). The invention relates to methods comprising administering insulin-like growth factor-I to a patient having a height which, at the time of treatment or prior to initial treatment with IGF-1, is at least about 2 standard deviations below normal for a subject of the same age and gender, a blood level of insulin-like growth factor-I that, and at the time of treatment or prior to initial treatment with IGF-1, is below normal mean levels, usually at least about 1 standard deviations below normal mean levels, for age and gender.

33 Claims, 1 Drawing Sheet

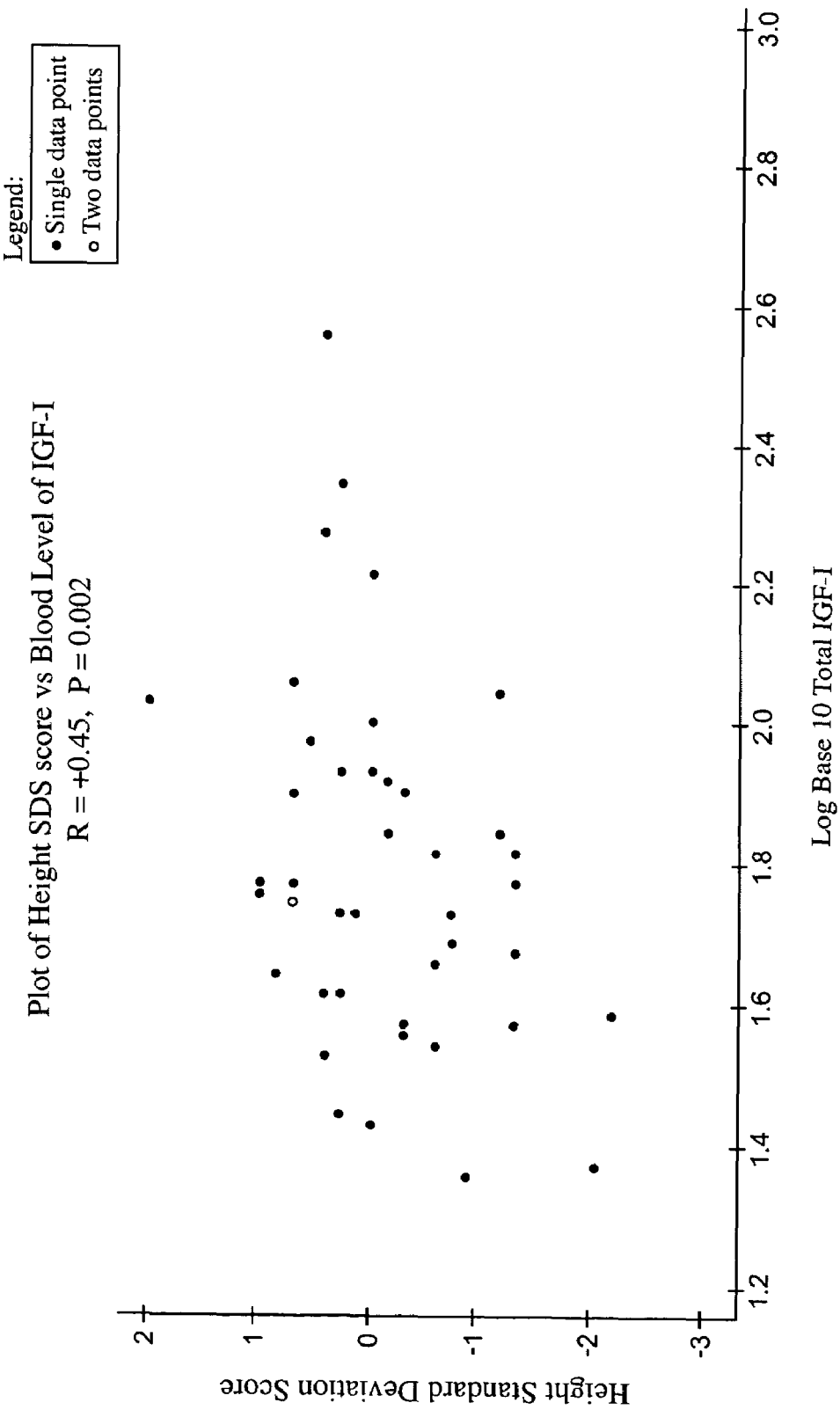

METHODS FOR TREATMENT OF INSULIN-LIKE GROWTH FACTOR-1 (IGF-1) DEFICIENCY

CROSS-REFERENCE TO RELATED APPLICATION

This application claims the benefit of U.S. Provisional Application No. 60/502,579, filed Sep. 12, 2003, which application is incorporated herein by reference in its entirety.

FIELD OF THE INVENTION

The present invention relates to methods and compositions for increasing the growth rates, alleviating the symptoms, or improving the metabolism of human patients having insulin-like growth factor-1 deficiency.

BACKGROUND OF THE INVENTION

The American Academy of Pediatrics and the American Academy of Clinical Endocrinology define short stature based on height as more than two standard deviations below the average population height. A child with short stature is shorter than 97.5% of children of a similar age and gender and typically attains final adult heights of no more than approximately 5'4" for boys and 4'11" for girls. It is estimated that 380,000 children in the U.S. with short statue are referred to pediatric endocrinologists for evaluation.

Children with short stature who are referred for evaluation and possible treatment continue to pose a dilemma for specialists despite decades of dedicated research. For patients with no demonstrable cause for their growth failure, a workup usually ensues which first seeks to differentiate between normal variation, in which the child should reach an adult height concordant with that of his family, and pathologic conditions. In cases of marked short stature, in which the predicted adult height is also low, it often becomes necessary to test the status of the growth hormone (GH)-insulin-like growth factor (IGF) axis.

Patients with abnormalities in the GH-IGF axis have a number of possible etiologies. They can present with GH deficiency (GHD), at times attributable to congenital or acquired central nervous system (CNS) lesions affecting the hypothalamus or pituitary, which is almost invariably accompanied by low IGF-1 levels in children. Alternatively, they can present "primary IGF deficiency" associated with low IGF-1 levels in the face of seemingly normal GH secretion. Because IGF-1 is an essential mediator of GH's statural effects, primary IGF deficiency can have similar clinical outcomes to GH deficiency. Such cases of primary IGF deficiency, in otherwise healthy and well-nourished patients, are likely to be caused by a defect somewhere in the GH-IGF axis downstream from the secretion of GH. This type of GH insensitivity is as yet unexplained in most cases, although it has been associated with mutations affecting the extra-cellular domain of the GH receptor in 1-5% of idiopathic short stature (ISS) children and adults, with mutations in Stat5b, with mutations in the acid labile subunit (ALS), or with mutations or polymorphisms in the IGF-1 gene itself.

GH deficiency is well recognized as a disease requiring replacement therapy with GH for short stature and in adults for body composition, bone density, cardiac function and for well being. By contrast, low IGF levels, in the presence of normal GH secretion, has been previously usually associated only with a rare disease, recognized as Laron syndrome or growth hormone insensitivity syndrome (GHIS).

Most patients with Laron syndrome or GHIS lack growth hormone receptor binding activity and have absent or very low GH-binding protein (GHBP) activity in blood. Such patients have a mean height standard deviation score (SDS) of about −5 to −6, are resistant to GH treatment, and have increased serum concentrations of GH and low serum concentrations of insulin-like growth factor (IGF-1). As children they show a statural growth response to treatment with IGF-1.

The disease of short stature due to partial GH receptor defects was traditionally seen as primarily a disease characterized by a low GHBP level rather than a low IGF-1 level, with IGF-1 levels being only at the low end of the normal range. Specifically, the patient is defined as having a height of at least about 2 standard deviations or more below the normal mean for a corresponding age and gender (at least −2.0 SD below the mean), a serum level of high-affinity growth hormone binding protein that is at least 2 standard deviations below normal mean levels, a serum level of IGF-1 that is below normal mean levels, and a serum level of growth hormone that is at least normal.

The importance of this classification of the various factors affecting short stature is shown in the relative numbers of patients who are: 1) IGF-1 deficient and GH deficient and 2) IGF-1 deficient and GH sufficient. Current literature would predict that many more children and adults would be IGF-1 deficient due to GH deficiency than would be IGF-1 deficient and GH sufficient.

Unlike GH deficiency (GHD), IGF-1 deficiency (IGFD) has not been recognized or appreciated as a disease with endocrine origins and in need of replacement therapy. Thus, there remains a need in the art for methods of treatment of IGF-1 deficient children and adults who do not have Laron syndrome or partial growth hormone insensitivity syndrome.

The present invention addresses these needs.

Literature

Literature of interest includes: U.S. Pat. No. 5,824,642; Salmon W D Jr. et al., 1957, J Lab Olin Med, 49:825-36; Liu, J-L and LeRoith, D, 1999, Endocrinology 140:5178-84; Lupu, F et al., 2001, Dev Biol 229:141-62; Zhou, Y et al., 1997, Proc Natl Acad Sci USA 94:13215-20; and Juul, 2003, GH and IGF Research 13: 113-170. Van Wyk J J. The Somatomedins: biological actions and physiological control mechanisms in Hormonal Proteins and Peptides, ed CH Li, 12:81-175, Orlando, Fla.: Academic Press; Clemmons D R et al., 1984, Clin Endocrinol Metab 13:113-43; Clemmons D R et al., 1979, N Engl J Med 301:1138-42; Clemmons D R et al., 1986, Olin Endocrinol Metal 15:629-51); Liu, J-L and LeRoith, D, 1999, Endocrinology 140:5178-84; Lupu, F et al., 2001, Dev Biol 229:141-62; Zhou, Y et al., 1997, Proc Natl Acad Sci USA 94:13215-20).

SUMMARY OF THE INVENTION

The present invention provides methods and compositions for increasing the growth rates, alleviating the symptoms, or improving the metabolism of human patients having insulin-like growth factor-1 deficiency (IGFD). The invention relates to methods comprising administering insulin-like growth factor-1 to a patient having a height which, at the time of treatment or prior to initial treatment with IGF-1, is at least about 2 standard deviations below a normal mean for a corresponding age and gender, a blood level of IGF-1 that, and at the time of treatment or prior to initial treatment with IGF-1, is below normal mean levels, usually at least about 1 standard deviations below normal mean levels for a corresponding age and gender.

The present invention is based, in part, on the discovery of a patient population that can benefit from IGF-1 supplementation. Such patients are identified as having low IGF-1 blood levels, i.e., blood levels of IGF-1 below normal mean levels, herein described as IGF-1 deficient ("IGFD"). The present invention establishes that short stature is more commonly related to a low IGF-1 level than it is associated with a low GH secretion. In addition, short stature correlates better with a low IGF-1 level than a low GHBP level. Just as standard deviation scores (SDS) are used by physicians to characterize height, an IGF-1 standard deviation score (IGF-1 SDS) indicates how many standard deviations a person's IGF-1 level is from the average level of the population of a similar age and gender. Further, it has been discovered that a significant number of children with extreme or severe short stature (−3 SDS for height) have at least normal GH secretion yet are very IGF deficient in that they have IGF-1 levels that are −3 SDS scores or less. These patients are characterized as suffering from severe primary IGFD.

Accordingly, in one aspect the invention features a method for treating a subject having insulin-like growth factor-1 deficiency (IGFD) comprising administering to a human pediatric subject an effective amount of insulin like growth factor-1 (IGF-1), wherein the subject is characterized as follows: a) at the time of treatment or prior to initial treatment with IGF-1, has or had a height at least about 2 standard deviations (SD) below a normal mean for a corresponding age and gender, and b) at the time of treatment or prior to initial treatment with IGF-1, has or had a blood level of IGF-1 at least about −1 SD below normal mean levels; wherein the subject does not have Laron syndrome or partial growth hormone insensitivity syndrome, and wherein said administering is effective to treat IGFD in the subject. In related embodiments, said administering alleviates at least one symptom of IGFD. In further related embodiments, said administering provides for an increase in growth rate or height.

In another aspect, the invention features a method for treating a subject having insulin-like growth factor-1 deficiency (IGFD) comprising administering to a human adult subject an effective amount of insulin like growth factor-1 (IGF-1), wherein the subject is characterized as follows: a) at the time of treatment or prior to initial treatment with IGF-1, has or had a height at least about 2 standard deviations (SD) below a normal mean for a corresponding age and gender, and 2) at the time of treatment or prior to initial treatment with IGF-1, has or had a blood level of IGF-1 at least about −1 SD below normal mean levels; wherein the subject does not have Laron syndrome or partial growth hormone insensitivity syndrome, and wherein said administering provides for treatment of IGFD in the subject. In related embodiments, said administering alleviates at least one symptom of IGFD.

In yet another aspect, the invention features a method for achieving at least normal insulin-like growth factor-1 (IGF-1) levels for age and gender (e.g., at least or greater than −2 SD below normal mean levels, or within a range of about −2.0 to +2.0 SD from a normal mean) in an insulin-like growth factor-1 deficiency (IGFD) subject, comprising administering an effective amount of insulin-like growth factor (IGF-1) to the patient, wherein the patient is characterized as follows: a) subject, at the time of treatment or prior to initial treatment with IGF-1, has or had a height at least about 2 standard deviations (SD) below a normal mean for a corresponding age and gender, and b) the subject, at the time of treatment or prior to initial treatment with IGF-1, has or had a blood level of IGF-1 at least about −1 SD below normal mean levels; wherein the subject does not have Laron syndrome or partial growth hormone insensitivity syndrome, and wherein said administering achieves blood IGF-1 levels within a normal range for a corresponding age and gender in the subject.

In embodiments related to each of the above aspects of the invention, the subject is further characterized as having at least normal blood levels of growth hormone binding protein (GHBP) (e.g., within a range of about −2.0 to about +2.0 SD from a normal mean). In further related embodiments, the subject is further characterized as having a blood level of growth hormone (GH) which is at least normal. In still other embodiments, the subject has a blood level of IGF-1 that is at least about 2.0 SD below normal mean levels.

In one embodiment of particular interest, IGF-1 is administered in a dose of about 20 to 240 µg/kg/day, which IGF-1 can be administered subcutaneously.

In yet other aspects the invention features a method for treating a subject having a primary insulin-like growth factor-1 deficiency (IGFD) comprising administering to a human subject having primary insulin-like growth factor-1 deficiency (IGFD) an effective amount of insulin like growth factor-1 (IGF-1), wherein the subject is characterized as follows: a) at the time of treatment or prior to initial treatment with IGF-1, has or had a height at least about 2 standard deviations (SD) below a normal mean for a corresponding age and gender, b) the time of treatment or prior to initial treatment with IGF-1, has or had a blood level of IGF-1 at least about −1 SD below normal mean levels, and c) at a blood level of growth hormone (GH) which is at least normal, wherein the subject does not have Laron syndrome or partial growth hormone insensitivity syndrome, and wherein said administering provides for treatment of IGFD in the subject.

In still other aspects the invention features a method for achieving at least normal insulin-like growth factor-1 (IGF-1) levels for a corresponding age and gender (e.g., within the normal range of IGF-1 levels for a corresponding age and gender) in a primary insulin-like growth factor-1 deficiency (IGFD) subject, comprising administering an effective amount of insulin-like growth factor (IGF-1) to a human subject, wherein the patient is characterized as follows: a) the subject, at the time of treatment or prior to initial treatment with IGF-1, has or had a height at least about 2 standard deviations (SD) below the normal mean for a corresponding age and gender, b) the subject, at the time of treatment or prior to initial treatment with IGF-1, has or had a blood level of IGF-1 at least about −1 SD below normal mean levels, and c) that subject has a blood level of growth hormone (GH) which is at least normal; wherein the subject does not have Laron syndrome or partial growth hormone insensitivity syndrome, wherein said administering achieves normal blood IGF-1 levels (e.g., within the normal range) for a corresponding age and gender in the subject.

In embodiments related to the above aspects of the invention, the subject is further characterized as having at least normal blood level of growth hormone binding protein (GHBP). In still other embodiments, the subject has a blood level of IGF-1 that is at least about 2.0 SD below normal mean levels. In one embodiment of particular interest, IGF-1 is administered in a dose of about 20 to 240 µg/kg/day, which IGF-1 can be administered subcutaneously. In further related embodiments, said administering alleviates at least one symptom of IGFD. In still further related embodiments, the subject is a human pediatric subject and said administering provides for an increase in growth rate or height.

The present invention thus also encompasses methods for treating a patient with short stature having a blood level of IGF-1, which a the time of treatment or prior to initial treatment, is at least about 1 standard deviation (SD) below normal mean levels (usually greater than 1 SD below normal mean levels, with at least about 2.0 SD below normal mean levels being of particular interest); and a height which, at the time of treatment, or prior to initial treatment, is at least about 2 standard deviations (SD) below the normal mean for a corresponding age and gender. Without being bound by any theory, administration of IGF-1 increases the blood levels of IGF-1. In the case of a patient with IGFD, the methods have application where the patient does not have Laron syndrome or partial growth hormone insensitivity syndrome.

In related embodiments, the patient also has a blood level of growth hormone binding protein (GHBP) (e.g., mean or maximal) that is at least normal. In further related embodiments the patient also has a blood level of growth hormone (e.g., mean or maximum stimulated) which is at least normal. The administration of IGF-1 results in alleviating a symptom associated with IGFD, which include lipid abnormalities, decreased bone density, obesity, insulin resistance, decreased cardiac performance, decreased muscle mass, decreased exercise tolerance. Alleviation of such symptoms is of particular interest in adults. Where the IGFD patient is a child, of particular interest is administration of IGF-1 to provide for an increase in the patient's height and growth rate.

Accordingly, in one aspect, the invention provides a method for increasing the growth rate of a human subject (usually a pediatric subject) having primary IGFD comprising administering an effective amount of IGF-1 to said subject, whereby said subject has a height which, at the time of treatment or prior to initial treatment with IGF-1, is at least about 2 standard deviations (SD) below the normal mean for a corresponding age and gender, has a blood level of IGF-1 that, at the time of treatment or prior to initial treatment with IGF-1, is greater than 1 SD below normal mean levels, wherein the subject does not have Laron syndrome or partial growth hormone insensitivity syndrome, and wherein said administering is effective to increase growth rate of the subject. In related embodiments, the subject also has a mean or maximum stimulated blood level of growth hormone which is at least normal and/or at least normal blood levels of growth hormone binding protein. The invention is useful in the treating children of short stature to accelerate their growth to increase their height.

In another aspect, the invention provides a method for treating IGFD in an adult patient comprising administering an effective amount of IGF-1 to said patient, wherein said patient has a height which, at the time of treatment or prior to initial treatment with IGF-1, is at least about 2 SD below the normal mean for a corresponding age and gender, has a blood level of IGF-1 that, at the time of treatment or prior to initial treatment with IGF-1, is greater than 1 SD below normal mean levels, and has a mean or maximum stimulated level of growth hormone which is at least normal. In this aspect, the invention is useful in adults to alleviate the symptoms of their IGF deficiency.

In certain embodiments, the patient has a blood level of IGF-1 of at least −1.0 SD, at least 2.0 SD below normal mean levels.

In certain embodiments, the invention provides methods for increasing the growth rate or reducing the metabolic effects of IGF deficiency of a patient by administration of an effective amount of IGF-1 at 20 to 240 μg/kg/day. In certain embodiments, the IGF-1 is administered subcutaneously.

Definitions

Before describing the invention in greater detail, the following definitions are set forth to illustrate and define the meaning and scope of the terms used to describe the invention herein.

As used herein, "patient" refers to any mammal, including humans, bovines, ovines, porcines, canines and felines, in need of treatment. In certain embodiments, the patient is a human. In general, the methods of the invention are applicable to pediatric and adult patients.

As used herein, "insulin-like growth factor-1 deficiency", "IGF-1 deficiency", or "IGFD" refer to a condition associated with the following characteristics, a height of at least about 2 standard deviations (SD) below the normal mean level for the corresponding age and gender, a blood level of IGF-1 that is at least 1 SD below normal mean levels. In general, IGFD can be due to a resistance to GH action or as a result of GH deficiency (GHD). IGFD that is due to resistance to GH action is termed primary IGFD, while IGFD resulting from GHD is termed secondary IGFD. Primary IGFD is distinguished from secondary IGFD in that primary IGFD is associated with at least normal GH blood levels, while secondary IGFD is associated with low blood levels of GH.

Thus, primary IGFD refers to a condition associated with the following characteristics, a height of at least about 2 standard deviations (SD) below the normal mean for the corresponding age and gender, a blood level of IGF-1 that is below normal mean levels, and a mean or maximum stimulated blood level of growth hormone (GH) that is at least normal (e.g., normal GH blood levels or greater than normal GH blood levels). GHBP levels are generally within the normal range.

Pediatric primary IGFD refers to pediatric patients with IGFD, while Adult primary IGFD refers to adult patients with IGFD. Adult primary IGFD, is similar to pediatric primary IGFD and is associated with a height of at least 2 SD below the normal mean for the corresponding age and gender, a blood level of IGF-1 that is at least 2 SD below the normal mean for the corresponding age and gender, and normal growth hormone levels. Adult primary IGFD patients have increased blood pressure, decreased cardiac performance, cardiac disease, renal disease impaired exercise performance, decreased muscle mass, decreased bone density, obesity and abnormalities of carbohydrate and lipid metabolism. Pediatric patients with primary IGFD are capable of having their height or growth rate increased, while adult patients are no longer capable of achieving a greater height. In certain embodiments, the subject methods do not encompass treating pediatric primary IGFD patients who have a blood level of high affinity growth hormone binding protein that is at least 2 SDs below normal mean levels and do not have Laron syndrome.

The term "concentration in blood", such as in the phrases "IGF-1 concentration in blood" or "IGFBP-3 concentration in blood", refers to a concentration of an agent (e.g., IGF-1 or IGFBP-3) obtained in whole blood or in a fluid obtained from blood, such as plasma or serum.

As used herein, "short stature" means a subject who has a height standard deviation score of about ≦2 SD below that of the normal mean for an individual of the same age and gender.

As used herein, the term "Laron syndrome" refers to a patient exhibiting complete lack of growth hormone receptor (GHR) function or complete growth hormone insensitivity syndrome (GHIS). Such patients have a mean height standard deviation score (SDS) of about −5 to −6 and respond to treatment with IGF-1. In patients with defects in the extracellular domain of the GHR, the lack of functional GHBP in the circulation can serve as a marker for the GH insensitivity. Additional common symptoms of "Laron syndrome" include small face and jaw, depressed nasal bridge, frontal bossing, obesity, high-pitched voice, and hypoglycemia in early childhood. Biochemically, Laron syndrome patients are characterized by having increased blood concentrations of GH and low blood GHBP concentrations, but low blood concentrations of IGF-1.

As used herein, "partial growth hormone insensitivity syndrome", or "partial GHIS" refers to a syndrome wherein the patient responds to the same doses of GH as that given to GH-deficient patients, but does not respond as well. This syndrome is further characterized in that the patient has a height of at least about 2 standard deviations below the normal mean for a corresponding age and gender, preferably in the range of about 2 to about 4 standard deviations or more below the normal mean for a corresponding age and gender (e.g., a SD of −2.0 or −4.0), has a blood level of high-affinity GHBP that is at least 2 standard deviations (typically about 2 to about 4 standard deviations) below the normal mean level for humans, has a blood level of IGF-1 that is below the normal mean level for humans, and has a mean or maximum stimulated blood level of GH that is at least normal. Mean blood levels are the mean of measurements in the patient.

As used herein, "IGF-1" refers to insulin-like growth factor-1 from any species, including bovine, ovine, porcine, equine, avian, and preferably human, in native-sequence or in variant form, and from any source, whether natural, synthetic, or recombinant.

Suitable for use in the subject methods is human native-sequence, mature IGF-1, for example, without an N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-1 is recombinantly produced and is available for clinical investigations (see, e.g., EP 123,228 and 128,733). The term "rhIGF-1" refers to recombinant human IGF-1.

As used herein, reference to "variants" or "analogs, homologs and mimics" of IGF-1 embraces compounds which differ from the structure of native IGF-1 by as little as the replacement and/or deletion of one or more residues thereof, to compounds which have no apparent structural similarity. Such compounds in all instances, however, have substantially the same activity as native IGF-1. Thus, "analogs" refers to compounds having the same basic structure as IGF-1, but differing in several residues; "homologs" refers to compounds which differ from native IGF-1 by the deletion and/or replacement of a limited number of residues; and "mimics" refers to compounds which have no specific structural similarity with respect to IGF-1 (indeed, a mimic need not even be a polypeptide), but such compound will display the biological activity characteristic of IGF-1 and/or stimulate endogenous IGF-1 production by the body or increase the amount of endogenous IGF-1 available to bind to IGF-1 receptors.

Suitable for use in the present invention are IGF-1 variants described in U.S. Pat. No. 5,077,276 issued Dec. 31, 1991; U.S. Pat. Nos. 5,164,370; 5,470,828; in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-1, des(1-3)-IGF-1, or des-IGF-1). Other compounds are the IGF-1 displacers compounds as described below, and in U.S. Pat. Nos. 6,121,416, 6,251,865, and 6,420,518.

As used herein, an "IGF binding protein" or "IGFBP" refers to a protein or polypeptide normally associated with or bound or complexed to IGF-1 or IGF-2, whether or not it is circulatory (i.e., in blood (e.g., serum) or tissue). Such binding proteins do not include receptors. This definition includes IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., 1995, Proc Natl Acad Sci USA, 92: 4472-4476 and Oh et al., J Biol Chem, 271: 30322-30325 (1996). PSF is described in Yamauchi et al., 1994, Biochem J, 303:591-598. ESM-1 is described in Lassalle et al., 1996, J Biol Chem, 271: 20458-20464. For other identified IGFBPs, see, e.g., EP 375,438 published Jun. 27, 1990; EP 369,943 published May 23, 1990; WO 89/09268 published Oct. 5, 1989; Wood et al., 1988, Mol Endocrinol, 2: 1176-1185; Brinkman et al., 1988, EMBO J, 7: 2417-2423; Lee et al., 1988, Mol Endocrinol, 2:404-411; Brewer et al., 1988; Biochem Biophys Res Comm, 152: 1289-1297; EP 294,021 published Dec. 7, 1988; Baxter et al., 1987, Biochem Biophys Res Comm, 147: 408-415; Leung et al., 1987, Nature, 330: 537-543; Martin et al., 1986, J Biol Chem, 261:8754-8760; Baxter et al., 1988, Comp Biochem Physiol, 91B: 229-235; WO 89/08667 published Sep. 21, 1989; WO 89/09792 published Oct. 19, 1989; and Binkert et al., 1989, EMBO J, 8: 2497-2502.

As used herein, "active", "bioactive", "biologically active" or "free" IGF-1 in the context of changing blood and tissue levels of endogenous IGF-1 refers to IGF-1 that binds to an IGF receptor or an insulin receptor, or a hybrid IGF/insulin receptor, or to an IGF binding protein, or otherwise causes a biological activity of endogenous or exogenous IGF-1 to occur.

As used herein, "high-affinity growth hormone binding protein" or "high-affinity GHBP" refers to the extracellular domain of the GHR that circulates in blood and functions as a GHBP in several species (Ymer et al., 1985, Mol. Cell. Endocrinol. 41:153; Smith et al., 1988, Endocrinology 123: 1489-1494; Emtner et al., 1990, Acta Endocrinologica (Copenh.), 122:296-302), including man (Baumann et al., 1986, J. Clin. Endocrinol. Metab., 62:134-141; EP 366,710 published 9 May 1990; Herington et al., 1986, J. Clin. Invest., 77:1817-1823; Leung et al., 1987, Nature 330:537-543. A second BP with lower affinity for GH has also been described that appears to be structurally unrelated to the GHR (Baumann et al., 1990, J. Clin. Endocrinol. Metab. 70:680-686. Various methods exist for measuring functional GHBP in blood, with the preferred method being a ligand-mediated immunofunctional assay (LIFA) described by Carlsson et al (1991, J. Clin. Endocrinol. Metab. 73:1216) and U.S. Pat. No. 5,210,017.

As used herein, "increasing the growth rate of a patient" includes not only the situation where the patient attains a similar ultimate height as GH-deficient patients treated with GH (i.e., patients diagnosed with GHD) or IGF-1 deficient patients treated with IGF-1, but also refers to a situation where the patient catches up in height at a similar growth rate as GH-deficient patients treated with GH or IGF-1 deficient patients treated with IGF-1, or achieves adult height that is close to the target height range, i.e., an ultimate height more consistent with their genetic potential as determined by the mid-parental target height.

As used herein, "alleviating a symptom of IGFD" refers to achieving a therapeutic benefit for a symptom associated with IGF-1 deficiency. Symptoms of IGFD patients include, but are not limited to, deincreased growth rate and height, increased blood pressure, decreased cardiac performance, cardiac disease, renal disease, neurological disease, impaired exercise performance, decreased muscle mass, decreased bone density, obesity and abnormalities of carbohydrate and lipid metabolism. Thus, alleviating symptoms of IGFD results in increased growth rates and height, bone density, bone structure, improved renal and cardiac function, and improved glucose control and body composition.

As used herein, "treatment" or "treating" refers to inhibiting the progression of a disease or disorder, e.g., short stature or IGFD, or delaying the onset of a disease or disorder, e.g., short stature or IGFD, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect may be prophylactic in terms of completely or partially preventing a disease or condition, or a symptom thereof and/or may be therapeutic in terms of a partial or complete cure for a disease or disorder and/or adverse affect attributable to the disease or disorder. "Treatment," as used herein, covers any treatment of a disease or disorder in a mammal, such as a human, and includes: decreasing the risk of death due to the disease; preventing the disease of disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease. Therapeutic benefits of the present invention include, but are not necessarily limited to, reduction of risk of onset or severity of disease or conditions associated with short stature or IGFD.

As used herein, a "therapeutically effective amount" refers to that amount of the compound sufficient to treat or manage a disease or disorder, e.g., short stature or IGFD. A therapeutically effective amount may refer to the amount of a compound that provides a therapeutic benefit in the treatment or management of a disease or disorder. Further, a therapeutically effective amount with respect to a compound of the invention means that amount of compound alone, or in combination with other therapies, that provides a therapeutic benefit in the treatment or management of a disease or disorder. The term can encompass an amount that improves overall therapy, reduces or avoids unwanted effects, or enhances the therapeutic efficacy of or synergies with another therapeutic agent.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, using a penetration enhancer other than DMSO. In other embodiments, the pharmaceutical compositions are suitable for administration by a route other than transdermal administration.

As used herein, the phrase "pharmaceutically acceptable carrier" refers to a carrier medium that does not interfere with the effectiveness of the biological activity of the active ingredient. Said carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These pharmaceutical compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharmaceutical Sciences* by E. W. Martin. Examples of suitable pharmaceutical carriers are a variety of cationic polyamines and lipids, including, but not limited to N-(1(2,3-dioleyloxy)propyl)-N,N,N-trimethylammonium chloride (DOTMA) and diolesylphosphotidylethanolamine (DOPE). Liposomes are suitable carriers for gene therapy uses of the invention. Such pharmaceutical compositions should contain a therapeutically effective amount of the compound, together with a suitable amount of carrier so as to provide the form for proper administration to the subject. The formulation should suit the mode of administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

As used herein, the phrase "pharmaceutically acceptable salts" refers to salts prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

As used herein, the phrase "mean or maximum stimulated blood level of GH" means a GH level of about 5 ng/ml in adults and about 10 ng/ml in children as measured by a radioimmunoassay following a GH stimulation test wherein a compound is administered that causes the release of GH.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "an individual" includes one or more individuals, and reference to "the method" includes reference to equivalent steps and methods known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citation or discussion of a reference herein shall not be construed as an admission that such is prior art to the present invention.

The invention will now be described in more detail.

BRIEF DESCRIPTION OF THE DRAWINGS

FIG. 1 is a graph depicting a plot of Height SDS vs. Blood Level of IGF-1 in adult patients previously characterized as suffering from Type 2 diabetes mellitus.

DETAILED DESCRIPTION OF THE INVENTION

The present invention is based on the surprising finding that IGF-1 administration increases the statural growth of certain pediatric patient populations not previously known to be amenable to treatment with IGF-1 to achieve a more normal height (e.g., toward or within the normal range for a corresponding age and gender). While not being bound by a particular theory, while the level of Growth Hormone binding protein (GHBP) has been found to reflect the state of the actual GH receptor, it is not a good indicator of intracellular signaling pathways "downstream" from the event of GH receptor binding. Thus, there are surprisingly many more pediatric patients who have evidence of GH resistance than can be identified by only measuring the level of GHBP. In view of the discoveries described herein, it is now estimated that a surprisingly large number of children, approximately 60,000 children in the U.S. and Western Europe suffer from primary insulin-like growth factor deficiency (IGFD). Moreover, approximately 12,000 children in the U.S. and Europe are afflicted by Severe Primary IGFD, defined as children who have a Height SDS of at least minus three ($\leq-3$) below the normal mean for a corresponding age and gender (i.e., at least 3 or more SD below), with IGF-1 SDS of at least minus three ($\leq-3$) below the normal mean for a corresponding age and gender (i.e., at least 3 or more SD below) and levels of growth hormone that are at least within the normal range. If left untreated, these children suffering from Severe Primary IGFD will attain final adult heights of no more than approximately 5'1" for boys and 4'9½" for girls.

Accordingly, a large number of adults suffer from the adverse metabolic effects of life-long IGFD. At least 120,000 individuals in the U.S. and Western Europe suffer from Adult Primary IGFD. Adult Primary IGFD is typically characterized by life-long IGF-1 deficiency. This disorder is similar to Pediatric Primary IGFD and is associated with a height SDS of at least minus two ($\leq-2$) below the normal mean for a corresponding age and gender (i.e., at least 2 or more SD below), IGF-1 SDS of at least minus two (≦-2) below the normal mean (i.e., at least 2 or more SD below), and normal growth hormone levels. Adult IGFD patients have increased blood pressure, decreased cardiac performance, cardiac disease, renal disease, impaired exercise performance, decreased muscle mass, decreased bone density, obesity and abnormalities of carbohydrate and lipid metabolism. Replacement therapy with rhIGF-1 will have beneficial effects with respect to these metabolic and functional abnormalities.

An association between adult height and mortality from coronary heart disease (CHD) has been detected in several studies. The very large "Nurses health study" a prospective cohort of 121,700 U.S. female nurses aged 30-55 years, showed that height is inversely related to risk of coronary heart disease in women (Rich-Edwards et al., 1995, Am J Epidemiol. 142:909-17). Moreover, a recent study relating short stature to clinical procedures in 1,046 men, showed that the shorter men had a higher prevalence and greater severity of angiographically verified CHD (Nwasokwa et al, 1997, Am Heart J 133:147-52). Recently it has been shown that short stature is an independent risk factor for coronary heart disease (Forsen et al., 2000, J Intern Med. 248:326-32). These authors speculate about, but rule out, a deficiency of growth hormone as being a possible cause of the original short stature and the subsequent adverse effects on the heart. In addition, these authors do not speculate as to the possibility that IGFD might be the cause of the short stature and the coronary heart disease in these patients with short stature.

Another large study in Europe showed that short stature is associated with several metabolic disorders and that skeletal disproportion is associated with diabetes in men while confirming the association of short stature with coronary heart disease in women (Han et al., 1997, Eur J Clin Nutr. 51:804-9).

Furthermore, there is also a relationship between short stature and renal disease. A recent study measured the level of albumin in urine of 3,960 patients who were 40 years old and older (Metcalf et al., 1997, Int Journal of Obesity 21: 203-210). Microalbuminuria was defined as being present if there was greater than 28 mg/dl of albumin in the urine based on reference value from the normal population. The height of the individuals was also measured. Persistent microalbuminuria is predictive of diabetic nephropathy (renal disease) and of increased morbidity and mortality from cardiovascular disease. In these patients short stature was a significant predictor of increased urinary albumin excretion. Other studies have found a similar relationship (Gould et al., 1993, Br Med J 306:240-243). Metcalf et al. do not explain the basis for this relationship between height and a marker of renal disease. Because of the unexpected relationship described in the present specification between blood IGF-1 level and height, an explanation can be provided for these findings.

There is a large literature showing that IGF-1 affects the kidney in terms of both structure and function (Clark and Roelfsema, 2001, J Am Soc Nephrol. 12:1297-306). Therefore it can be seen that the above relationship between height and renal disease can be explained by the blood levels of IGF-1 varying with height. Therefore patients who are short and have low blood levels of IGF-1 (patients who are IGFD) are patients who would benefit most from treatment with IGF-1. In these IGFD patients replacement therapy with IGF-1 would be expected to reduce microalbuminuria, improve renal function, and reduce mortality.

It is clear that it is not height itself that has these effects but the underlying mechanisms that affect height. Forsen et al. state that the factors and mechanisms through which the factors act remain unknown. It has been shown in obese patients and in Type 2 diabetics that overall IGF-1 blood levels are relatively normal (Frystyk et al, 1999, Diabetes Metab Res Rev. 15:314-22). However there is little information on the IGF-1 levels in adults, or in short adults with cardiovascular disease or heart disease.

The low IGF-1 level in the presence of levels of GH that are at least normal is indicative of GH resistance. This concept of growth hormone insensitivity syndrome (GHIS), of a low GHBP level being indicative of GH resistance, pre-supposed that GH resistance would be associated with a low blood level of the GHBP and therefore a low number of GH receptors. However, it is now recognized as part of this invention that many more patients than previously described are short due to GH resistance. This is because, as described herein, the primary measures of GH resistance is the blood IGF-1 concentration and the blood GH level rather than the blood level of the GHBP. Without being limited to any one theory, GH resistance is more likely due to defects in intracellular GH signaling than to a deficit in the number or function of the GH receptors on cells themselves.

Therefore it is clear that the GHBP level in blood is only indicative of the degree of GH resistance in a minority of patients. A better indicator, or blood marker, or biochemical characteristic of a patient, of the degree of GH resistance (as seen in individuals suffering from short stature) is the blood IGF-1 level. Therefore, replacement therapy with IGF-1 is better gauged and administered to patients who are IGF-1 deficient than those that are GHBP deficient.

The level of blood IGF-1 also has profound metabolic effects. Therefore, as children with IGFD become adults, they continue to suffer from the effects of IGF-1 deficiency. Since after puberty the growth plates in the long bones fuse and additional cartilage and bone growth and increase in height can no longer occur, rhIGF-1 replacement therapy does not cause growth in adults. However, low levels of blood IGF-1 are also frequently associated with other metabolic disorders, including lipid abnormalities, decreased bone density, obesity, insulin resistance, decreased cardiac performance, decreased muscle mass, decreased exercise tolerance and well being. These disorders typically become increasingly apparent after a prolonged period of IGF-1 deficiency, as occurs in adulthood. Accordingly, this disorder is referred to as Adult IGFD.

It is an object of the present invention to provide methods and compositions for increasing the height and growth rates and improving the metabolism and function of patients with IGFD. In certain embodiments, as in the case of IGFD subjects, the goal of treatment is to restore biologically active IGF-1 levels or to increase tissue exposure to IGF-1, to those found within normal subjects of the same age and gender, and, in children, thereby increase the heights and growth rate of these subjects to within the normal range for subjects of the same age and gender, while, in adults, reducing the incidence of the adverse metabolic and functional defects which characterize IGFD.

Administration of IGF-1

The present invention provides methods and compositions for increasing the height and growth rates and improving the metabolism of patients with IGFD by administering to the patients an effective amount of IGF-1. In some embodiments, native human IGF-1 is used. In other embodiments, IGF-1 variants are used. In yet other embodiments, IGF-1 displacers are used.

Suitable for use in the subject methods are IGF-1 variants. IGF-1 variants can be designed that retain efficient binding to the type I IGF receptor, yet would have reduced binding to serum carrier proteins, e.g. IGFBPs. In one aspect, the design of these variants is based on the observation that insulin does not bind to serum carrier proteins. See U.S. Pat. No. 4,876,242, issued Oct. 24, 1989, herein expressly incorporated by reference in its entirety. Evidence from synthetic, insulin-like two chain analogs suggests that amino acids of IGF-1 responsible for carrier protein binding are in the B region of IGF-1. Therefore a synthetic gene for human IGF-1 can be modified to encode an IGF-1 variant in which the first 16 amino acids of hIGF-1 are replaced by the first 17 amino acids of the B chain of human insulin. The synthetic gene is then placed in a yeast recombinant DNA expression system and the peptide analog which is produced by the modified yeast cells is extracted therefrom and purified. Additional modifications of the IGF-1 molecule have been carried out leading to additional analogs, all of which have substantial IGF-1 type I receptor binding and reduced binding to serum carrier proteins.

Other IGF-1 variants and analogs well known in the art are also suitable for use in the subject methods. Such variants include, for example, the variant having resides 1-69 of authentic IGF-1, further described in WO 96/33216, and the two-chain IGF-1 superagonists which are derivatives of the naturally occurring single-chain IGF-1 having an abbreviated C domain, further described in EP 742,228. IGF-1 analogs are of the formula: BC$^n$, A wherein B is the B domain of IGF-1 or a functional analog thereof, C is the C domain of IGF-1 or a functional analog thereof, n is the number of amino acids in the C domain and is from about 6 to about 12 amino acids, including about 8 to about 10 amino acids, and A is the A domain of IGF-1 or a functional analog thereof.

Also suitable for use in the subject methods are functional mutants of IGF-1 that are well known in the art. Such functional mutants include those described in Cascieri et al. (1988, Biochemistry 27:3229-3233), which discloses four mutants of IGF-1, three of which have reduced affinity to the Type I IGF receptor. These mutants are: (Phe$^{23}$, Phe$^{24}$, Tyr$^{25}$)IGF-1 (which is equipotent to human IGF-1 in its affinity to the Types 1 and 2 IGF and insulin receptors), (Leu$^{24}$)IGF-1 and (Ser$^{24}$)IGF-1 (which have a lower affinity than IGF-1 to the human placental Type I IGF receptor, the placental insulin receptor, and the Type I IGF receptor of rat and mouse cells), and desoctapeptide (Leu$^{24}$)IGF-1 (in which the loss of aromaticity at position 24 is combined with the deletion of the carboxyl-terminal D region of hIGF-1, which has lower affinity than (Leu$^{24}$)IGF-1 for the Type I receptor and higher affinity for the insulin receptor). These four mutants have normal affinities for human serum binding proteins.

Also suitable for use with the subject methods include structural analogs of IGF-1 well known in the art. Such structural analogs include those described in Bayne et al. (1988, J Biol Chem 264:11004-11008), which discloses three structural analogs of IGF-1: (1-62)IGF-1, which lacks the carboxyl-terminal 8-amino-acid D region of IGF-1; (1-27,Gly$^4$,38-70)IGF-1, in which residues 28-37 of the C region of IGF-1 are replaced by a four-residue glycine bridge; and (1-27,Gly$^4$,38-62) IGF-1, with a C region glycine replacement and a D region deletion. Peterkofsky et al. (1991, Endocrinology, 128: 1769-1779) discloses data using the Gly$^4$ mutant of Bayne et al., supra. U.S. Pat. No. 5,714,460 refers to using IGF-1 or a compound that increases the active concentration of IGF-1 to treat neural damage.

Other structural analogs include those described in Cascieri et al. (1989, J Biol Chem, 264: 2199-2202) discloses three IGF-1 analogs in which specific residues in the A region of IGF-1 are replaced with the corresponding residues in the A chain of insulin. The analogs are: (Ile$^{41}$, Glu$^{45}$, Gln$^{46}$, Thr$^{49}$, Ser$^{50}$, Ile$^{51}$, Ser$^{53}$, Tyr$^{55}$, Gln$^{56}$)IGF-1, an A chain mutant in which residue 41 is changed from threonine to isoleucine and residues 42-56 of the A region are replaced; (Thr$^{49}$,Ser$^{50}$,Ile$^{51}$)IGF-1; and (Tyr$^{55}$, Gln$^{56}$) IGF-1.

IGF-1 point variants which bind to IGFBP-1 or IGFBP-3, thus inhibiting the interaction of endogenous IGF-1 with IGFBPs are also suitable for use with the subject methods and are described in U.S. Pat. No. 6,509,443.

In another embodiment, the level of IGF-1 is increased by administering a compound that prevents or inhibits the interaction of IGF-1 with its binding proteins, such as a IGF-1 agonist molecules that are capable of effectively inhibiting the interaction of IGF-1 with its binding proteins, thereby allowing IGF-1 to bind to the IGF receptor for activity. Such IGF-1 agonists suitable for use in the subject methods include those described in See U.S. Pat. No. 6,251,865, issued Jun. 26, 2001, herein expressly incorporated by reference in its entirety. These IGF-1 agonist molecules can effectively displace IGF-1 bound to IGFBP. The IGF binding proteins (IGFBPs) are a family of at least six proteins (See Jones and Clemmons, 1995, Endocr Rev, 16: 3-34; Bach and Rechler, 1995, Diabetes Reviews, 3: 38-61), with other related proteins also possibly binding the IGFs. The IGFBPs bind IGF-1 and IGF-2 with varying affinities and specificities. See Jones and Clemmons, supra; Bach and Rechler, supra. For example, IGFBP-3 binds IGF-1 and IGF-2 with a similar affinity, whereas IGFBP-2 and IGFBP-6 bind IGF-2 with a much higher affinity than they bind IGF-1. See Bach and Rechler, supra; Oh et al., 1993, Endocrinology, 132, 1337-1344.

Also suitable for use in the subject methods include binding molecules, other than a natural IGFBP, as described in WO 94/04569 than can prevent the binding of IGF-1 to a IGFBP by binding to IGF-1 and thereby enhancing the biological activity of IGF-1. In addition, other molecules that are capable of preventing or inhibiting the interaction of IGF-1 with its binding proteins includes ligand inhibitors of IGF-1, as disclosed in WO 97/39032.

Also suitable for use in the subject methods include IGF-1 point variants which bind to IGFBP-1 or IGFBP-3, thus inhibiting the interaction of endogenous IGF-1 with IGFBPs, which are further described in U.S. Pat. No. 6,509,443.

Also suitable for use in the subject methods include IGF displacers that are peptides discovered by phage display that are capable of inhibiting the interaction of an IGF with any one of its binding proteins, as further described in, e.g., U.S. Pat. Nos. 6,420,518; 6,251,865; and 6,121,416, all of which are hereby expressly incorporated by reference in their entireties.

Small molecule nonpeptide inhibitors can also release biologically active IGF-1 from the IGF-1/IGFBP-3 complex. For example, isoquinoline analogues have been found to be effective (See Chen et al., 2001, J Med Chem 44:4001-10). Additional compounds can be found using high throughput screening and the IGFBP Radioligand binding assay as described in Chen et al., 2001.

Other IGF-1 agonists include, but are not limited to; small molecules; synthetic drugs; peptides; polypeptides; proteins; nucleic acids (e.g., DNA and RNA nucleotides including, but not limited to, antisense nucleotide sequences, triple helices and nucleotide sequences encoding biologically active proteins, polypeptides or peptides); antibodies; synthetic or natural inorganic molecules; mimetic agents; and synthetic or natural organic molecules.

In addition, the present invention contemplates using gene therapy for administering IGF-1 to patients. Generally, gene therapy can be used to increase (or overexpress) IGF-1 levels in the mammal using a recombinant vector to express an IGF-1 gene. Also, gene therapy can be used to express a nucleic acid encoding an IGF agonist compound, if it is a peptide. As another example, antisense oligonucleotides can be used to reduce the expression of an IGFBP. Other examples of gene therapy can be contemplated by one of routine skill in the art.

There are two major approaches to introducing the nucleic acid (optionally contained in a vector) into the subject's cells for purposes of gene therapy: in vivo and ex vivo. For in vivo delivery, the nucleic acid is injected directly into the subject, usually at the site where increased levels of IGF-1 is required. For ex vivo treatment, the subject's cells are removed, the nucleic acid is introduced into these isolated cells and the modified cells are administered to the subject either directly or, for example, encapsulated within porous membranes which are implanted into the subject. See, e.g. U.S. Pat. Nos. 4,892,538 and 5,283,187, both of which are herein expressly incorporated by reference in their entireties.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

An example of an in vivo nucleic acid transfer technique includes transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., 1987, J Biol Chem, 262:4429-4432; and Wagner et al., 1990, Proc Natl Acad Sci USA, 87: 3410-3414. For a review of the currently known gene marking and gene therapy protocols, see Anderson et al., 1992, Science, 256: 808-813 and WO 93/25673 and the references cited therein.

Combination Therapy

Combination therapy with IGF-1 and one or more other appropriate reagents, such as those that increase total IGF-1 level in the blood or enhance the effect of the IGF-1, is also contemplated by this invention. In one embodiment, these additional reagents generally allow an excess of blood IGF-1 over the amount of IGFBPs in blood or the IGF-1 to be released from IGFBPs, and include growth-promoting agents.

Growth-promoting agents for this purpose include, but are not limited to, GH secretagogues that promote the release of endogenous GH in mammals to increase concentrations of the IGF in the blood. Examples include TRH, diethylstilbestrol, theophylline, enkephalins, E series pro staglandins, peptides of the VIP-secretin-glucagon-GRF family, and other GH secretagogues such as GHRP-6, GHRP-1 as described in U.S. Pat. No. 4,411,890, and benzo-fused lactams such as those disclosed in U.S. Pat. No. 5,206,235. See also, e.g., WO 96/15148 published May 23, 1996. Other growth-promoting agents include GHRPs, GHRHs, GH and their analogs. For example, GHRPs are described in WO 95/17422 and WO 95/17423 both published Jun. 29, 1995; Bowers, J, 1993, Pediatr Endocrinol, 6:21-31; and Schoen et al., 1993, Annual Reports in Medicinal Chemistry, 28: 177-186. GHRHs and their analogs are described, for example, in WO 96/37514 published Nov. 28, 1996.

The reagent can be co-administered sequentially or simultaneously with IGF-1, and may be administered in the same, higher, or a lower dose than if used alone depending on such factors as, for example, the type of reagent used, the purpose for which the reagent and compound are being used, and clinical considerations. In addition, other means of manipulating IGF status, such as regimens of diet or exercise, are also considered to be combination treatments as part of this invention.

In another embodiment, IGF-1 is appropriately administered together with any one or more of its binding proteins, for example, IGFBP-1, IGFBP-2, IGFBP-3, IGFBP-4, IGFBP-5, or IGFBP-6. Without being bound by a mechanism, co-administration of IGF-1 and an IGFBP may provide a greater response than IGF-1 alone by increasing the half-life of IGF-1.

A binding protein suitable for use is IGFBP-3, which is described in U.S. Pat. No. 5,258,287 and by Martin and Baxter, 1986, J Biol Chem, 261: 8754-8760. This glycosylated IGFBP-3 protein is an acid-stable component of about 53 Kd on a non-reducing SDS-PAGE gel of a 125-150 Kd glycoprotein complex found in human plasma that carries most of the endogenous IGFs and is also regulated by GH.

The administration of the IGF binding protein with IGF-1 may be accomplished by the method described in U.S. Pat. No. 5,187,151. Briefly, the IGF-1 and IGFBP are administered in effective amounts by subcutaneous bolus injection in a molar ratio of from about 0.5:1 to about 3:1, including about 0.75:1 to about 2:1, such as about 1:1.

Subjects Suitable for Treatment

Subjects suitable for treatment with the methods disclosed herein include subjects that suffer from IGFD. In general, the IGFD patient population has, for example, the following characteristics: 1) a height at least about 2 standard deviations (SD) below the normal mean for the corresponding age and gender, and 2) a blood level of IGF-1 that is at least 1 SD below normal mean levels. In one embodiment, the present invention encompasses methods for treating IGFD children who do not have a blood level of high-affinity growth hormone binding protein that is at least 2 SDs below normal mean levels, and do not have Laron syndrome. In another embodiment, the present invention encompasses methods for treating IGFD children who do not have a blood level of high-affinity growth hormone binding protein that is at least 2 SDs below normal mean levels, and do not have partial growth hormone insensitivity syndrome (partial GHIS).

In one embodiment, the present invention encompasses methods for treating IGFD children who have a mean or maximum stimulated blood level of growth hormone which is at least within the normal range.

In certain embodiments, the subject suffering from IGFD has a height, for example, of at least about 2.0 SD below the normal mean for a corresponding age and gender, at least about 2.5 SD below the normal mean for a corresponding age and gender (i.e., −2.5 SD), or at least about 3.0 SD below the normal mean for a corresponding age and gender, usually at least about usually between about 2.0 SD and about 3.0 SD below the normal mean for a corresponding age and gender, between about 2.5 SD and about 3.0 SD below the normal mean for a corresponding age and gender, or at least about 3.0 SD below the normal mean for a corresponding age and gender. In certain embodiments, the subject suffering from IGFD has a blood level of IGF-1 at least 1 SD below the normal range for their corresponding age and gender. IGF-1 deficient subjects can have blood levels of IGF-1 that are, for example, at least about 2.0 SD below normal mean levels for a corresponding age and gender, at least about 3.0 SD below normal mean levels for a corresponding age and gender, usually from about 2.0 SD to about 3.0 SD below normal mean levels for the corresponding age and gender. An IGFD patient may also have blood levels of high affinity growth hormone binding protein less than the normal mean, but not more than 2SD below the normal mean. In certain embodiments, the blood level of high-affinity growth hormone binding protein is between normal mean levels and −0.5 SD below normal mean levels, between normal mean levels and 0.5 SD below normal mean levels, between 0.5 SD and 1.0 SD below normal mean levels, between 1.0 SD and 1.5 SD below normal mean levels, or between 1.5 SD and 2.0 SD below normal mean levels.

Short stature patients who will benefit from increased IGF-1 levels can be identified using routine methods known in the art. IGF-1 levels can be detected in blood. A genetic abnormality associated with IGF-1 can be detected using standard genetic assays. A marker for a local IGF-1 deficit (such as levels of IGFBP-1) can be detected using routine assays.

Measuring IGF levels in a biological fluid such as a body or blood fluid can be done by any means, including RIA and ELISA. For example, total IGF-1 in the blood can be determined by commercially available radioimmunoassays (Medgenix Diagnostics, Brussels, Belgium; IGF-1 RIA Kit, Nichols Institute, San Juan Capistrano, Calif.) especially after the extraction of the blood sample using acid ethanol to remove binding proteins which interfere with the detection of the IGF-1 by competing with anti-IGF-1 antibody. IGFBP can be measured using commercially available immunoradiometric assays (IRMAs) for measuring IGFBP-1 and IGFBP-3 (Diagnostic System Laboratories Inc., Webster, Tex.).

Another method involves measuring the level of "free" or active IGF in blood. For example, one method is described in U.S. Pat. No. 5,198,340, herein expressly incorporated by reference in its entirety. An additional method is described in U.S. Pat. No. 6,251,865, issued Jun. 26, 2001, herein expressly incorporated by reference in its entirety, for detecting endogenous or exogenous IGF bound to an IGF binding protein or the amount of a compound that binds to an IGF binding protein and does not bind to a human IGF receptor bound to an IGF binding protein or detecting the level of unbound IGF in a biological fluid. This method comprises: (a) contacting the fluid with 1) a means for detecting the compound that is specific for the compound (such as a first antibody specific for epitopes on the compound) attached to a solid-phase carrier, such that in the presence of the compound the IGF binding sites remain available on the compound for binding to the IGF binding protein, thereby forming a complex between the means and the IGF binding protein; and 2) the compound for a period of time sufficient to saturate all available IGF binding sites on the IGF binding protein, thereby forming a saturated complex; (b) contacting the saturated complex with a detectably labeled second means which is specific for the IGF binding protein (such as a second antibody specific for epitopes on the IGFBP) which are available for binding when the compound is bound to the IGF binding protein; and (c) quantitatively analyzing the amount of the labeled means bound as a measure of the IGFBP in the biological fluid, and therefore as a measure of the amount of bound compound and IGF binding protein, bound IGF and IGF binding protein, or active IGF present in the fluid.

U.S. Pat. Nos. 5,593,844 and 5,210,017, herein expressly incorporated by reference in their entireties, disclose a ligand-mediated immunofunctional binding protein assay method that can be used to quantitate the amount of IGFBP in a liquid sample by the use of antibodies, where complex formation takes place between one of these binding proteins and the ligand that binds to it.

The quantitative technique mentioned above using antibodies, called the ligand-mediated immunofunctional method (LIFA), is described for determining the amount of IGFBP by contact with IGF in U.S. Pat. No. 5,593,844, herein expressly incorporated by reference in its entirety.

Dosage and Schedule of Administration

Selection of the therapeutically effective dose can be determined (e.g., via clinical trials) by a skilled artisan, such as a clinician or a physician, based upon the consideration of several factors which will be known to one of ordinary skill in the art. Such factors include, for example, the particular form of IGF-1, and the compound's pharmacokinetic parameters such as bioavailability, metabolism, half-life, and the like, which is established during the development procedures typically employed in obtaining regulatory approval of a pharmaceutical compound. Further factors in considering the dose include the disease or condition to be treated, the benefit to be achieved in a subject, the subject's body mass, the subject's immune status, the route of administration, whether administration of the compound or combination therapeutic agent is acute or chronic, concomitant medications, and other factors known by the skilled artisan to affect the efficacy of administered pharmaceutical agents.

The identification and treatment of IGFD as a new condition has direct parallels with the identification and treatment of GHD. It has been noted by others (Drake et al., 2001, *Endocrine Reviews* 22: 425-450) that it was only the advent of modem neuro-radiological imaging techniques in 1989 that allowed the diagnosis of GH deficiency in adults to be established with certainty. It was this identification of patients with small or damaged pituitaries and low IGF-1 levels and low GH levels that greatly assisted in establishing a diagnosis of adult GHD. It was also therefore only relatively recently that it was recognized that there is a characteristic clinical syndrome associated with failure of spontaneous GH secretion and that the use of recombinant GH to reverse many of its features has become established.

In terms of how to treat with IGF-1 it is instructive to consider the methods by which GH replacement therapy is practiced. In adults there is no biological marker of GH action that is the equivalent of height or growth in a child. Therefore it is difficult to judge the efficacy of GH replacement in adults. The assessment of optimal GH replacement is made difficult by the occurrence of side effects if too high doses are administered. GH treatment is therefore begun at low doses, with doses then being increased to the dose that is the final maintenance dose. It is further very instructive that appropriate GH dosing in adults is best determined by the measurement of blood levels of IGF-1, so as to avoid supra-physiological levels of IGF-1.

In addition the use of growth hormone antagonists has also been instructive. In states of GH excess (such as acromegaly) the current aim of treatment with growth hormone antagonists is to reduce IGF-1 levels into the normal range. The measurement of blood levels of IGF-1 has been characterized as a sensitive and specific indicator for the presence acromegaly and the persistence of disease after therapy (Freda, 2003, GH and IGF Research 13:171-184).

There are now normative data on blood levels of IGF-1 that have been measured in many thousands of patients so that IGF-1 standard deviation scores (IGF-1 SDS) have been established (Juul, GH and IGF Research 13, 113-170, 2003). Just as in children these normative data are age and gender adjusted to establish the normative range for a subject at a given age and gender.

It is clearly a parallel argument that appropriate replacement therapy in adults (and in children) is to establish doses of IGF-1 that raise IGF-1 levels into the age adjusted normal range. There has been much recent work to establish the normal range of IGF-1 levels in children and adults (Juul, GH and IGF Research 13, 113-170, 2003, herein expressly incorporated by reference in its entirety).

In some embodiments, the total pharmaceutically effective amount of IGF-1 administered parenterally per dose will be in the range of about 10 µg/kg/day to about 400 µg/kg/day, including about 20 µg/kg/day to about 200 µg/kg/day, such as, about 40 µg/kg/day to about 100 µg/kg/day, of subject body weight, although, this will be subject to a great deal of therapeutic discretion. Preferred doses for adults are in the range of about 10 µg/kg/day to about 160 µg/kg/day. Other doses of interest for adults are in the range of about 10 µg/kg/day to about 180 µg/kg/day In some embodiments of particular interest, 20 to 240 µg/kg/day IGF-1 is administered to the subject. The IGF-1 may be administered by any means, including injections (single or multiple, e.g., 1-4 per day) or infusions. In certain embodiments, the IGF-1 is administered once or twice per day by subcutaneous injection. If a slow release formulation is used, typically the dosages used (calculated on a daily basis) will be less, up to one-half of those described above.

The present invention further provides methods for increasing growth rate using a pharmaceutical composition of IGF-1, and a pharmaceutically acceptable carrier. Suitable pharmaceutically acceptable carriers include essentially chemically inert and nontoxic pharmaceutical compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such pharmaceutical compositions should contain a therapeutically effective amount of the compound, together with a suitable amount of carrier so as to provide the form for proper administration to the subject. The formulation should suit the mode of administration. For example, oral administration requires enteric coatings to protect the compounds of the invention from degradation within the gastrointestinal tract. In another example, the compounds of the invention may be administered in a liposomal formulation, particularly for nucleic acids, to shield the compounds from degradative enzymes, facilitate transport in circulatory system, and effect delivery across cell membranes to intracellular sites.

In another embodiment, a pharmaceutical composition comprises a IGF-1 protein, and/or one or more therapeutic agents; and a pharmaceutically acceptable carrier. In one embodiment, a pharmaceutical composition, comprising a IGF-1 protein, with or without other therapeutic agents; and a pharmaceutically acceptable carrier, is at an effective dose.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In some embodiments, the composition is formulated in accordance with routine procedures as a pharmaceutical composition adapted for subcutaneous injection or intravenous administration to humans. Typically, pharmaceutical compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

In certain embodiments, the formulation for IGF-1 is that described in U.S. Pat. No. 5,681,814. This formulation is as follows: about 2 to about 20 mg/ml of IGF-1, about 2 to about 50 mg/ml of an osmolyte, about 1 to about 15 mg/ml of at least one stabilizer, and a buffer (such as an acetic acid salt buffer, or sodium acetate) in an amount such that the composition has a pH of about 5 to about 5.5. Optionally, the formulation may also contain a surfactant, preferably in an amount of about 1 to about 5 mg/ml, such as about 1 to about 3 mg/ml.

In some embodiments, the osmolyte is an inorganic salt at a concentration of about 2-10 mg/ml or a sugar alcohol at a concentration of about 40 to about 50 mg/ml, the stabilizer is benzyl alcohol, phenol, or both, and the buffered solution is an acetic acid salt buffered solution. In further embodiments, the osmolyte is an inorganic salt, such as sodium chloride.

In yet further embodiments, the formulation includes about 8 to about 12 mg/ml of IGF-1, about 5 to about 6 mg/ml of sodium chloride, benzyl alcohol as the stabilizer in an amount of about 8 to about 10 mg/ml and/or phenol in an amount of about 2 to about 3 mg/ml, and about 50 mM sodium acetate buffer so that the pH is about 5.4. Optionally, the formulation contains polysorbate as a surfactant in an amount of about 1 to about 3 mg/ml.

Pharmaceutical compositions adapted for oral administration may be provided, for example, as capsules or tablets; as powders or granules; as solutions, syrups or suspensions (in aqueous or non-aqueous liquids); as edible foams or whips; or as emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semi-solid, or liquid polyols, etc. Solutions and syrups may comprise, for example, water, polyols and sugars.

An active agent intended for oral administration may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

Pharmaceutical compositions adapted for parenteral administration include, but are not limited to, aqueous and non-aqueous sterile injectable solutions or suspensions, which may contain antioxidants, buffers, bacteriostats and solutes that render the pharmaceutical compositions substantially isotonic with the blood of an intended recipient. Other components that may be present in such pharmaceutical compositions include water, alcohols, polyols, glycerine and vegetable oils, for example. Compositions adapted for parenteral administration may be presented in unit-dose or multi-dose containers, for example, sealed ampules and vials, and may be stored in a freeze-dried (lyophilized) condition requiring the addition of a sterile liquid carrier, e.g., sterile saline solution for injections, immediately prior to use. Extemporaneous injection solutions and suspensions may be prepared from sterile powders, granules and tablets. Such pharmaceutical compositions should contain a therapeutically or cosmetically effective amount of a compound which increases IGF-1 blood levels, together with a suitable amount of carrier so as to provide the form for proper administration to the subject. The formulation should suit the mode of administration.

Pharmaceutical compositions adapted for transdermal administration may be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols or oils. A topical ointment or cream is preferably used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable pharmaceutical compositions. In these pharmaceutical compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, pharmaceutical compositions adopted for nasal administration may comprise liquid carriers such as, for example, nasal sprays or nasal drops. These pharmaceutical compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided, for example, as pessaries, tampons, creams, gels, pastes, foams or spray formulations.

Suppositories generally contain active ingredients in the range of 0.5% to 10% by weight. Oral formulations preferably contain 10% to 95% active ingredient by weight.

In yet another embodiment, IGF-1 may be administered using long-acting IGF-1 formulations that either delay the clearance of IGF-1 from the site or cause a slow release of IGF-1 from, e.g., an injection or administration site. The long-acting formulation that prolongs IGF-1 plasma clearance may be in the form of IGF-1 complexed, or covalently conjugated (by reversible or irreversible bonding) to a macromolecule such as a water-soluble polymer selected from PEG and polypropylene glycol homopolymers and polyoxyethylene polyols, i.e., those that are soluble in water at room temperature. See, e.g., U.S. Pat. No. 5,824,642, hereby expressly incorporated by reference in its entirety. Alternatively, the IGF-1 may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethylene glycerol is the same backbone occurring in, for example, animals and humans in mono-, di-, and triglycerides. The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1-C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

The IGF-1 may also be coupled to a receptor or antibody or antibody fragment for administration.

Administration of the pharmaceutical compositions of the invention includes, but is not limited to, oral, intravenous infusion, subcutaneous injection, intramuscular, topical, depo injection, implantation, time-release mode, intracavitary, intranasal, inhalation, intratumor, intraocular, and controlled release. The pharmaceutical compositions of the invention also may be introduced parenterally, transmucosally (e.g., orally), nasally, rectally, intravaginally, sublingually, submucosally, or transdermally. Preferably, administration is parenteral, i.e., not through the alimentary canal but rather through some other route via, for example, intravenous, subcutaneous, intramuscular, intraperitoneal, intraorbital, intracapsular, intraspinal, intrasternal, intra-arterial, or intradermal administration. The skilled artisan can appreciate the specific advantages and disadvantages to be considered in choosing a mode of administration. Multiple modes of administration are encompassed by the invention. For example, a IGF-1 protein is administered by subcutaneous injection, whereas a combination therapeutic agent is administered by intravenous infusion. Moreover, administration of one or more species of IGF-1 proteins, with or without other therapeutic agents, may occur simultaneously (i.e., co-administration) or sequentially. For example, a IGF-1 protein is first administered to increase sensitivity to subsequent administration of a second therapeutic agent or therapy. In another embodiment, the periods of administration of one or more species of IGF-1 protein, with or without other therapeutic agents may overlap. For example, a IGF-1 protein is administered for 7 days, and a second therapeutic agent is introduced beginning on the fifth day of IGF-1 protein treatment, and treatment with the second therapeutic agent continues beyond the 7-day IGF-1 protein treatment. The IGF-1 can also be administered intermittently in a cyclical manner as described in U.S. Pat. No. 5,565,428.

In one embodiment, a pharmaceutical composition of the invention is delivered by a controlled-release or sustained release system. For example, the pharmaceutical composition may be administered using intravenous infusion, an implantable osmotic pump, a transdermal patch, liposomes, or other modes of administration. In one embodiment, a pump may be used (See, e.g., Langer, 1990, Science 249: 1527-33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (See, e.g., Langer, Science 249:1527-33 (1990); Treat et al., 1989, in *Liposomes in the Therapy of Infectious Disease and Cancer*, Lopez-Berestein and Fidler (eds.), Liss, New York, pp. 353-65; Lopez-Berestein, ibid., pp. 317-27 International Patent Publication No. WO 91/04014; U.S. Pat. No. 4,704,355). In another embodiment, polymeric materials can be used (See, e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228:190; During et al., 1989, Ann. Neurol. 25:351; Howard et al., 1989, J. Neurosurg. 71:105). Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (see Sidman et al., 1983, Biopolymers, 22:547-556), poly(2-hydroxyethyl methacrylate) (Langer et al., 1981, J. Biomed Mater Res, 15:167-277), and Langer, 1982, Chem Tech, 12:98-105), ethylene vinyl acetate (Langer et al., supra) or poly-D-(-)-3-hydroxybutyric acid (EP 133, 988). Sustained-release IGF-1 compositions also include liposomally entrapped IGF-1. Liposomes containing IGF-1 are prepared by methods known per se: DE 3,218,121; Epstein et al., 1985, Proc Natl Acad Sci USA, 82:3688-3692; Hwang et al, 1980, Proc Natl Acad Sci USA, 77: 4030-4034; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol percent cholesterol, the selected proportion being adjusted for the optimal IGF-1 therapy.

In yet another embodiment, a controlled release system can be placed in proximity of the target. For example, a micropump may deliver controlled doses directly into the brain, thereby requiring only a fraction of the systemic dose (See, e.g., Goodson, 1984, in *Medical Applications of Controlled Release*, vol. 2, pp. 115-138). IGF-1 could be delivered directly into the peritoneal cavity to preferentially expose visceral fat to drug.

In one embodiment, it may be desirable to administer the pharmaceutical composition of the invention locally to the area in need of treatment; this may be achieved, for example, and not by way of limitation, by local infusion during surgery, topical application (e.g., in conjunction with a wound dressing after surgery), injection, by means of a catheter, by means of a suppository, or by means of an implant. An implant can be of a porous, non-porous, or gelatinous material, including membranes, such as sialastic membranes, or fibers.

IGF-1 can be administered before, during, and/or after the administration of one or more therapeutic agents. In yet another embodiment, there can be a period of overlap between the administration of IGF-1 and/or one or more therapeutic agents.

The present invention may be better understood by reference to the following non-limiting Examples, which are provided only as exemplary of the invention. The following examples are presented to more fully illustrate the preferred embodiments of the invention. They should in no way be construed, however, as limiting the broader scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Interrelationships Among Various Measures Related to the GH-IGF Axis

Data from large surveillance studies of the use of GH, such as the National Cooperative Growth Study (NCGS) can be helpful in determining patient populations that will respond to IGF-1 treatment, especially with associated substudies looking at referred but untreated patients and using centralized assay results. One such substudy of the NCGS (Substudy VI) noted that short children undergoing hormonal testing were found as a group to have low IGF-1 levels (IGF-1 SDS=−1.7±1.7, mean±SD) despite relatively normal maximum stimulated GH levels. One of the goals of this substudy was to explore the interrelationships among various measures related to the GH-IGF axis, including stimulated GH, GHBP, IGF-1 and IGF binding protein 3 (IGFBP-3). The data surprisingly showed a substantial proportion of referred short children have primary IGFD, that is, are GH sufficient but IGF-1 deficient.

NCGS substudy VI was designed to evaluate the hormonal basis of short stature. This study was limited to untreated subjects undergoing evaluation for the hormonal basis of short stature. The protocol-stated objectives were to 1) identify patients with undetectable or subnormal blood GHBP levels for possible further evaluation, as well as determine the GHBP levels for subgroups of children with short stature; and 2) define the relationship of GHBP to GH, IGF-1, and IGFBP-3 levels in blood.

Patient Population

Subjects included in the study were evaluated for the hormonal basis of their short stature. Only patients for whom baseline specimens were supplied for GH stimulation test(s), IGF-1, IGFBP-3 and GHBP were included. Patients currently receiving GH therapy were excluded.

Study Design

Upon enrollment, a single plasma sample was collected for the measurements of GHBP, IGF-1 and IGFBP-3. This was accompanied by up to 8 blood samples for measurement of GH levels from one or two standard GH provocative stimulation tests. An amendment to the protocol provided for a single follow-up blood sample for the repeat measurements of GHBP, IGF-1 and IGFBP-3 at approximately one year after baseline for untreated subjects, or after approximately one year of therapy in subjects subsequently treated with GH.

Laboratory Methods

All specimens were sent to a single laboratory (Nichols Institute) for centralized determination of hormone levels. Growth hormone was measured using the Hybritech immunoradiometric assay (IRMA) using a monoclonal antibody to GH. Such IRMA assays return values that are roughly half the value obtained using radioimmunoassay for GH (a GH value of 5 ng/ml in an IRMA roughly equals a value of 10 ng/ml in an RIA). IGF-1 was measured using a radioimmunoassay (RIA, Nichols Institute) following acid-ethanol extraction. IGFBP-3 was measured by RIA with recombinant standard and tracer. GHBP was measured by ligand-mediated immunofunctional assay (LIFA) (see, e.g., U.S. Pat. No. 5,210,017).

Statistical Analysis

Subjects were included in analyses if enrollment age was between 0 and 20 years and all four baseline laboratory measurements were available. Data are presented as mean±standard deviation (SD) except where noted. Data are presented as SD scores (SDS), adjusting for age and gender using normative data provided for each measurement or assay.

Results

A total of 6447 subjects were evaluated in four cohorts:
1) all 6447 subjects;
2) subjects with height SDS<−2, IGF-1 SDS<−2, and maximum stimulated GH<10 ng/mL;
3) subjects with height SDS<−2, IGF-1 SDS<−2, and maximum stimulated GH>10 ng/mL; and
4) subjects with height SDS<−3, IGF-1 SDS<−3, and maximum stimulated GH>10 ng/mL.

All Subjects

For the entire cohort in the study (n=6447), the mean age at the time of baseline diagnostic evaluation was 10.1±4.0 yr, with a mean bone age of 8.0±3.8 yr and mean bone age delay=2.2±1.6 yr. The mean height SDS was −2.5±1.1 and mean BMI SDS was −0.5±1.4. At baseline, 68% of subjects were male and 76% were pre-pubertal. As expected, 77% of subjects had no defined etiology of their short stature at baseline. Only 75% of the subjects who were referred for short stature had height SDS<−2 (n=4663), and 87% had a serum IGF-1 that was below normal SDS<0 (normal mean), and 39% of these children with short stature, or 1955 children, had a serum IGF-1 of SDS<−2.

The median maximum stimulated (peak) GH level for the 6447 subjects was 7.5 µg/L, using the Hybritech assay, equivalent to 15 µg/L by radioimmunoassay (RIA). The mean value for IGF-1 SDS was −1.7±1.7 and for IGFBP-3 SDS was −1.0±1.6. However, mean GHBP SDS was −0.2±1.2. The log peak GH levels were positively correlated with IGF-1 SDS and IGFBP-3 SDS (r=0.29, 0.28, respectively) and negatively with GHBP SDS (r=−0.19). A stronger correlation existed between IGF-1 SDS and IGFBP-3 SDS (r=0.65). GHBP SDS was weakly positively correlated with IGF-1 SDS and IGFBP-3 SDS (r=0.15, 0.12, respectively).

Short Subjects with Low IGF-1 and Low GH

Subjects in cohort 2 had height SDS<−2, IGF-1 SDS<−2 and maximum stimulated GH<10 ng/mL. These subjects constitute the "GH deficient" group (n=776 of 1955, or 39% of the short IGF deficient group). In this cohort, 64% were male and 82% were prepubertal. Mean IGF-1 SDS was −3.8±1.8, with 58% having IGF-1 SDS<−3. This group is the growth hormone deficient group and are called GHD.

Short Subjects with Low IGF-1 and GH Levels that are at Least Normal

Subjects in the cohort 3 had height SDS<−2, IGF-1 SDS<−2 and maximum stimulated GH>10 ng/mL. These subjects constitute the "IGF deficient/GH sufficient" group (n=1179 of the 1955 patients, or 61% of the short IGF deficient group). This cohort had a greater percentage of males (71%) compared to cohort 2. Mean IGF-1 SDS was −3.0±0.9, with 41% having IGF-1 SDS<−3. Height SDS was <−3 in 39%. This is the group referred to in this study as primary IGFD.

Very Short Subjects with Very Low IGF-1 and GH Levels that are at Least Normal

Subjects in the cohort 4 had height SDS<−3, IGF-1 SDS<−3 and maximum stimulated GH>10 ng/mL. These subjects constitute a group of extreme short stature and extreme IGF deficiency (n=212, or 18% of IGFD subjects). This is the group referred to in this study as severe primary IGFD.

Discussion

The management of children with marked short stature, despite decades of study, remains a largely subjective undertaking that varies among countries, between institutions and even among physicians working at the same institution. The criteria for using growth-promoting therapies, which currently consist primarily of recombinant human growth hormone (rhGH) and gonadotropin releasing hormone (GnRH) agonists, have included hormonal, auxologic, radiographic, genetic, ethical and economic factors. Aside from treating a causal underlying condition (such as hypothyroidism or precocious puberty) or using rhGH for specific, approved indications (such as Turner syndrome), the question of intervention often comes down to 1) is there a defect in the GH-IGF axis?; and 2) will final adult height be significantly compromised without treatment?

Tests for GH deficiency usually involve pharmacologic stimuli which differ in their mechanism of stimulating GH release. Only a very small proportion (about 5-10% of those who are referred to clinics for short stature) of children with short stature are GH deficient. However several studies have suggested that other abnormalities in the GH/IGF system might contribute to short stature in a significant number of non-GHD patients. For example, in many patients with short stature low IGF-1 levels are not associated with GH deficiency.

Data from large post-marketing surveillance studies, such as the Genentech National Cooperative Growth Study (NCGS) or Kabi International Growth Study (KIGS) indicate that a number of non-GH deficient children are receiving rhGH therapy, and that they represent a select group of patients with a degree of short stature similar to those classified as GH deficient. Many in the field feel that growth-promoting therapy for these patients is unnecessary on the grounds that they have "normal-variant" short stature, or simply some combination of "constitutional delay of growth and puberty" and "familial short stature." However, each of these classifications is dependent on demonstration that the GH-IGF axis is normal and furthermore, that final adult height is (or will be) within the mid-parental target range. On the contrary, patients being considered for GH treatment typically do not attain their genetic height potential, with or without GH treatment at standard doses. Furthermore, it appears that many have low IGF-1 levels.

Ultimately, deficiency of insulin-like growth factor I (IGF-1), the key mediator of most GH biologic actions, is critical to understanding abnormalities along the GH/IGF axis. Certainly, severe growth hormone insensitivity (Laron) syndrome is capable of causing growth failure equal to that seen in severe forms of GH deficiency, due to the similar end-result of profound IGF-1 deficiency. While normal IGF-1 levels are considered unusual in confirmed cases of GH deficiency, low IGF-1 levels are perhaps more common than one would expect in patients who are clearly GH sufficient. In contrast, this study shows that normal GH and abnormal IGF-1 is relatively common. Put another way, IGF-1 deficiency is relatively common in children who are GH sufficient.

In the absence of malnutrition or liver disease, IGF deficiency in an otherwise healthy individual may be explained by a defect in the GH-IGF axis. In GH sufficient patients, partial GH insensitivity may exist at the level of the GH receptor or downstream. In 1-5% of children with so-called idiopathic short stature, demonstrable lesions in the extracellular domain of the GH receptor have been found. Abnormalities in GH receptor signal transduction, as measured by tyrosine phosphorylation, have also been reported. Theoretically, other causes of isolated IGF deficiency or resistance could be due to gene defects affecting the Stat5B gene, IGF binding proteins, or the IGF receptor.

The cause of IGF deficiency in most otherwise healthy children is poorly understood. In cases where GH secretion is clearly normal or even elevated, the cause is necessarily some form of partial GH insensitivity, although the exact nature of this resistance to GH is unknown in most cases. Patients with ISS enrolled in clinical studies of GH therapy tend to have low GHBP levels and to respond poorly to standard doses of rhGH as compared with other short stature groups. However, normal GHBP levels were seen in this substudy of as yet untreated patients. Clearly, whatever selection process physicians initiate before placing such children on rhGH therapy, which may have included low IGF-1 levels, delayed bone age, and other factors, results in a group with clinical signs of GH resistance.

Recombinant human IGF-1 (rhIGF-1) therapy has thus far been successfully used in three extremely rare forms of profound IGF deficiency, involving defects of the GH receptor gene, the GH gene, or the IGF-1 gene. This study establishes that there are a substantially larger number of children with unexplained short stature who have some degree of IGF-1 deficiency, yet are GH sufficient. As GH deficiency is today treated with rhGH replacement therapy, there is a role for rhGF-1 replacement therapy in the patients who are IGF deficient.

Example 2

Relationship between Height and Blood Concentration of IGF-1

The aim of this study was to examine the relationship in adults between height and the blood concentration of IGF-1 and then treat the patients with rhIGF-1.

Subjects

Individuals who had previously been diagnosed as suffering from Type II diabetes mellitus (DM) were selected for study. The 44 subjects were men and women 30 to 70 years of age with a hemoglobin A1c level of greater than 8.0%. The subjects were all receiving treatment for hyperglycemia with oral medication(s) only.

Blood was drawn and height was measured. Total IGF-1 was measured by radioimunoassay after extracting the sample with acid-ethanol. Hemoglobin A1c levels were also measured. Systolic blood pressure was also measured.

The patients were then treated with rhIGF-1, as described in Example 1, at either 20 or 40 micrograms per kilogram twice daily by subcutaneous injection for 12 weeks.

Results

FIG. 1 shows the positive (r=+0.45) and highly statistically significant (p=0.002) relationship between the height standard deviation score (Height SDS) and the blood concentration of IGF-1 before treatment with rhIGF-1. The IGF-1 values are expressed as logarithms due to the concentrations not being normally distributed.

Treatment with rhIGF-1 reduced blood glucose levels and reduced hemoglobin A1c levels from 9.9 to 9.1%, a significant fall (p<0.001).

Treatment with rhIGF-1 at 20 micrograms/kg twice daily reduced systolic blood pressure from 140.4 to 130.9 after treatment a fall of 9 mm of Hg, a highly significant fall (p<0.001)

Conclusion

An unexpected result was obtained in that the serum concentration of IGF-1 was positively correlated with the height of the patient. A recent and exhaustive review of the factors affecting blood IGF-1 levels states that "[i]n adults, IGF-1 does not correlate with the endogenous GH secretion . . . " (Juul, 2003, GH and IGF Research 13:113-170). The review goes on to state that "other regulators of IGF-1 in adults must be considered." The factors considered by these authors are "body composition, physical activity, life style habits and changes in sex steroid levels." There is no mention of a relationship between height and IGF-1 levels in adults.

This surprising finding provides the first evidence that many of the factors such as cardiovascular disease, renal disease, diabetes and bone disease that have been shown to be associated with short stature are associated with low IGF-1 levels or IGFD.

In addition the data shows that replacement therapy in these patients has a significant effect on blood glucose, hemoglobin A1c, and blood pressure. These are all measures that reflect the diseases associated with short stature in adults. Therefore it is clear that replacement therapy with IGF-1 in these patients is effective and indicated. IGF-1 replacement would be therefore expected to have a significant impact on the many diseases that result from IGFD and short stature.

Example 3

Administration of rhIGF-1

An animal study was conducted administering rhIGF-1 for the life-time of animals to study the long-term effects of rhIGF-1 in normal animals.

It has been shown that the efficacy of GH is limited in humans with normal GH secretion. Such children with normal GH secretion (so-called patients with idiopathic short stature) show very small growth responses to GH. It might be predicted that the long-term efficacy of rhIGF-1 might be limited by such effects as rhIGF-1 causing an acceleration of bone age, which would cause the epiphyses of the long bones to close early which would limit the ability to grow, or of rhIGF-1 inhibiting GH secretion and thereby having a self-limiting effect on growth.

This Example shows a long-term study in animals that is equivalent to similar long-term treatment in growing children. Because the epiphyses of the long bones of rats stay open for a very long period relative to their life span, it is possible for rats to grow for most of their lives. The example used a broad range of doses of rhIGF-1 in a very large number of animals for a very long period.

Animals

Male and female Crl:CD®(SD)BR VAF/Plus®rats were obtained from the Portage, Mich., facility of Charles River Laboratories, Inc. The animals were 41 to 44 days old at initiation of treatment. The males weighed from 178 to 264 grams, and the females weighed from 131 to 199 grams at initiation of treatment.

The animals were housed individually (except for the first 3 days of acclimation when animals were group-housed) in stainless-steel, screen-bottom cages. Some animals were placed in polycarbonate cages during the study because of health problems.

Certified rodent diet (#5002 meal, PM® Feeds, Inc.) was provided except when animals were fasted. The diet was routinely analyzed by the manufacturer for nutritional components and environmental contaminants.

Water was provided ad libitum. Samples of the water are analyzed for specified microorganisms and environmental contaminants.

Acclimation

Four hundred fifty male rats and four hundred fifty female rats were acclimated for 14 days (with respect to the male animals) or 15 days (with respect to the female animals) before initiation of treatment. In general, animals appeared healthy. During acclimation, the animals were examined for abnormalities indicative of health problems, an ophthalmic examination was done, and body weights were recorded for all animals approximately 1 week before randomization and at randomization. Food consumption was recorded for all animals for approximately 1 week during acclimation.

Group Designations and Dose Levels

The animals were examined by a laboratory animal veterinarian and found to be suitable for study inclusion. Selection of animals for the study was based on clinical observation, body weights, ophthalmic examinations, and other data as appropriate. Animals were assigned to treatment groups using a blocking procedure designed to achieve body weight balance with respect to treatment group. At the time of randomization, the weight variation of the animals did not exceed ±2 standard deviations of the mean body weight for each gender. Group mean body weights were analyzed using Levene's test for homogeneity of variance at the 5.0% probability level and found to be homogenous. Animals were assigned to the study according to the following design.

TABLE 1

| Group | Dose Level (mg/kg/day)[a] | Dose Concentration (mg/mL) | No. of Animals Male | No. of Animals Female |
|---|---|---|---|---|
| Carcinogenicity Animals | | | | |
| 1 Vehicle | 0 | 0 | 75 | 75 |
| 2 Low (rhIGF-1) | 0.25 | 0.25 | 75 | 75 |
| 3 Mid 1 (rhIGF-1) | 1.0 | 1.0 | 75 | 75 |
| 4 Mid 2 (rhIGF-1) | 4.0 | 4.0 | 75 | 75 |
| 5 High (rhIGF-1) | 10.0 | 10.0 | 75 | 75 |
| Satellite Animals | | | | |
| 6 Vehicle | 0 | 0 | 15 | 15 |
| 7 Low (rhIGF-1) | 0.25 | 0.25 | 15 | 15 |
| 8 Mid 1 (rhIGF-1) | 1.0 | 1.0 | 15 | 15 |
| 9 Mid 2 (rhIGF-1) | 4.0 | 4.0 | 15 | 15 |
| 10 High (rhIGF-1) | 10.0 | 10.0 | 15 | 15 |

[a]The dose volume was 1 mL/kg. Individual doses were based on the most recently recorded body weights.

Results

Administration of rhIGF-1 caused an increase in body weight gain in males and females at all dose levels. The magnitude of this effect increased with increasing dose, although the effect for animals given 10.0 mg/kg/day was only slightly greater than that of those given 4.0 mg/kg/day. For males, the effect on mean body weight was generally statistically significant from week 6 throughout the majority of the study at the 10.0, 4.0, and 1.0 mg/kg/day dose levels; for males given 0.25 mg/kg/day, statistically significant changes were first apparent at week 22. For females, the effect on mean body weight was generally statistically significant throughout the majority of the study beginning at week 3 for animals given 10.0 and 4.0 mg/kg/day and week 6 for animals given 10.0 mg/kg/day. For females given 0.25 mg/kg/day, statistically significant changes generally were noted from week 20 to 63. The magnitude of the effect on body weight was marked for animals given 4.0 or 10.0 mg/kg/day. At the beginning of week 69, a time when survival for males and females given the high dose was at least 50%, mean body weights for males given 0.25, 1.0, 4.0, or 10.0 mg/kg/day were 109%, 116%, 123% and 129% of control values, respectively; for females this was 104%, 113%, 128% and 131% of control values, respectively. The increased body weight gain for test material-treated animals was consistent with increases in food consumption also noted in these groups.

Summary

The results show that in animals with normal GH secretion that rhIGF-1 had profound growth promoting activity. In contrast, GH treatment in humans with normal GH secretion had limited effects, as seen in studies where GH is given to children with idiopathic short stature, as opposed to the robust effect of GH treatment in GHD.

Example 4

A Study of Long-Term rhIGF-1 Treatment in Children with Short Stature Due to IGF Deficiency The objective of this study is to evaluate the efficacy and safety of long-term replacement therapy with rhIGF-1, in children with short stature due to IGF deficiency (Pediatric primary IGFD).

Significance to Human Health

Recombinant human IGF-1 has been used in clinical trials to treat the most severely affected cases of Primary IGF Deficiency (Laron Syndrome and several cases of deletion of the human GH gene). The height standard deviation score of such individuals in the untreated state usually declines with age because of profoundly low linear growth velocities. Doses from 40-120 µg/kg given twice daily by subcutaneous injection have been employed. The doses of 40-60 µg/kg have proven marginally effective with modest increases in height velocity that were generally insufficient to increase the height standard deviation scores, i.e., no "catch-up" growth is observed. Doses in the range of 80-120 µg/kg generally cause improvements in linear height velocity substantial enough to improve the height standard deviation scores and such improvements have been observed to persist for up to 10 years of treatment. The treatment effect of rhIGF-1 therapy is unknown in patients with less profound IGFD (e.g., those with heights and serum IGF standard deviation scores of minus 2 or less). Such subjects suffer from a degree of short stature for which growth hormone therapy is approved for subjects with growth hormone deficiency, Turner Syndrome, Intra-uterine growth retardation and Prader-Willi Syndrome. This trial is designed to determine if children with a similar degree of short stature (height less than −2 SD) and IGFD (blood IGF-1 less than −2 SD) will respond favorably to rhIGF-1 therapy.

Pharmacokinetic analyses of rhIGF-1 in normal adult subjects and in subjects with Types 1 and 2 diabetes strongly suggest that the disposition of administered rhIGF-1 is greatly influenced by the prevailing concentrations of the IGF binding proteins in serum, most notably the concentration of IGFBP-3. A highly significant relationship exists between serum IGFBP-3 concentrations and the clearance of administered rhIGF-1 such that low serum IGFBP-3 concentrations predict rapid clearance of rhIGF-1 and potentially diminish the effect of treatment.

Children with more modest degrees of Primary IGFD also have less IGFBP-3 deficiency than do subjects with Laron Syndrome. Accordingly, a more limited range of rhIGF-1 doses (50-100 µg/kg, twice daily) is employed in this trial design.

The most extreme form of IGFD is called GHIS, or Laron-type dwarfism (Laron Z et al., 1980, Ann Clin Res 12:269-77; Laron Z et al., 1966, Isr J Med Sci 2:152-55; Laron Z et al., 1968, Isr J Med Sci 4:883-94), and is transmitted as an autosomal recessive trait. It is most common among Asiatic Jews and other Middle Eastern people, but occurs sporadically in other ethnic groups. Although molecular heterogeneity of GH-receptor defects have been described (Amselem S et al., 1991, Trends Endocrinol Metab 21:35-40), affected individuals share the clinical characteristics of severe GH deficiency: they are short, grow at a slow rate, have immature facial features and body proportions, and have excess body fat. As in patients with GH deficiency, serum concentrations of IGF-1 are low. In contrast with GH deficiency, however, serum GH concentrations are elevated, stimulation of GH secretion produces a supra-normal response, and exogenously administered GH does not increase IGF-1 levels or produce the expected metabolic and growth responses. The basis of the GH resistance in this condition is defective (or absent) GH receptors on cell surfaces. In addition, circulating GH binding proteins, which are homologous to the extracellular domain of the GH receptor, are often undetectable in affected patients. Those in whom the serum GH binding protein is found are believed to have a defect in the transmembrane or intracellular domains of the GH receptor or to have a defect in the post-receptor pathway of GH action (Godowski P et al., 1989, Proc Natl Aced Sci (USA) 1989; 86:8083-7; Eshet R et al., 1984, Isr J Med Sci 20:8-11).

The form of IGFD addressed in this protocol occurs in children who have defects in the growth hormone signaling pathway in that their tissues respond to growth hormone poorly because they transduce the growth hormone signal very weakly. In addition to short stature, these children have a characteristic biochemical profile that includes high growth hormone levels and inappropriately low circulating levels of IGF-1. They would be expected to respond poorly to pharmacologic amounts of exogenous GH.

The data that rhIGF-1 is an effective form of replacement therapy for some GHIS patients is based upon in vitro studies with cell lines derived from Laron-type patients and in vivo studies in animals and normal adult humans. Erythroid progenitor cells and permanently transformed T-cell lines derived from patients with IGFD (Laron-type) have been shown to proliferate in response to 1-10 ng/ml of IGF-1 in vitro (Geffner M E et al., 1987, J Clin Endocrinol Metab 64:1042-6). In vivo infusion of human IGF-1 stimulates weight gain and linear growth in GH deficient mice (Van Buul-Offers S et al., 1986, Pediatr Res 20:825) and hypophysectomized rats. When infused into insulin-deficient rats, IGF-1 stimulates growth without aggravating hyperglycemia or glycosuria (Schoenle E et al., 1982, Nature 296:252). While slow continuous infusion of rhIGF-1 seems to be well tolerated (Zapf J et al., 1986, J Clin Invest 77:1768), administration of an IV bolus produces hypoglycemia, an anticipated insulin-like effect (Guler H-P et al., 1987, N Engl J Med 317:137).

Laron and colleagues (Laron Z et al., 1991, Clin Endocr 35:145-50) gave seven daily subcutaneous injections of recombinant IGF-1 in doses of 120 or 150 mg/kg/day to 10 subjects with GHIS (Laron-type). This resulted in a marked rise in serum type III procollagen, and decreases in plasma GH, serum cholesterol, serum SGOT, and serum LDH. A variable response of plasma insulin was observed, with some patients decreasing their fasting insulin concentrations while others experienced an increase.

Walker et al. (1991, N Engl J Med 324:1483-8) studied an 8.9-year-old boy with well-characterized Laron-type IGF-1 deficiency. The child had physical and biochemical features typical of the syndrome: severe growth failure; high serum GH; low IGF-1; absence of GH binding protein; failure to increase IGF-1 in response to short-term administration of GH; failure to show improved growth during a six-month trial of GH—therapy. This patient received an 11 day infusion of rhIGF-1 (Genentech) and was also observed for 8 days after the infusion. Whereas GH treatment had produced no metabolic effects, the IGF-1 infusion caused dramatic changes in a variety of metabolic parameters (Walker J L et al., 1991, N Engl J Med 324:1483-8). These results confirmed that most of the in vivo effects of GH are mediated through IGF-1 and that rhIGF-1 replacement can bypass the metabolic resistance to GH. In addition, these results suggest that there is a strong likelihood that rhIGF-1 will produce growth in patients with IGFD due to GH receptor defects. In addition to these metabolic effects, the study showed that rhIGF-1 infusion could produce fasting hypoglycemia (due to the insulin-like properties of this peptide) as well as blunt meal-induced insulin secretion resulting in postprandial hyperglycemia.

A treatment protocol was developed to determine whether IGF-1 therapy could sustain linear growth in patients with primary IGFD. Patients were maintained on doses required for optimal growth in the absence of side effects. The 120 microgram/kg dose of rhIGF-1 was well tolerated and gave plasma concentrations of IGF-1 in the normal range.

Research Plan

The aim of this protocol was to determine whether long-term administration of recombinant human insulin-like growth factor I (rhIGF-1), at doses ranging from 80 µg/kg to 120 µg/kg given BID, or TID, by subcutaneous injection to children with primary IGFD is safe and effective and can restore normal growth and metabolism to children with primary IGFD.

Subjects:

Patients with growth impairment due to primary IGFD were enrolled. Inclusion criteria included height of at least 2 SD below the normal mean for age; growth rate of less than the 50th percentile for age; plasma IGF-1 at 2 SD below the mean for age; age greater than 2 years; random or stimulated GH levels that are at least normal, which is defined as a GH level that is greater than or equal to 10 ng/ml. Exclusion criteria included active malignancy or any history of malignancy; growth failure due to other reasons; disorders of genitourinary, cardiopulmonary, gastrointestinal, or nervous system, other endocrine disorders, nutritional/vitamin deficiencies, or chondrodystrophies; treatment with any corticosteroids or other medications that influence growth; clinically significant EKG abnormality of a history of clinically significant cardiac arrhythmia.

Methods of Procedure:

Annual Visits:

Anthropometric measurements of height and weight were done by the same clinician; using standardized equipment. Blood pressure was also documented. Interim history was obtained including assessment for side effects of treatment.

Study drug medication records were reviewed. An ECHO was done to assess size and function of the heart. A renal ultrasound was done to monitor the size and growth of the kidneys. An audiogram and tympanometry was done to assess hearing. DEXA scan was performed to assess bone mineral content and body composition.

Treatment:

Subjects received replacement therapy with rhIGF-1 at doses ranging from 80-120 micrograms/kg, given subcutaneously BID, or TID, with a maximum total dose of 240 micrograms/kg daily. The dose chosen for each patient was based on patient tolerance and titrated to optimize growth.

If symptoms of hypoglycemia occurred, patients, and parents/guardians of patients were instructed to monitor home blood glucose levels using a home glucose analyzer. Caretakers were instructed to call the investigator for readings below 40 or above 200 mg/dl or for symptoms of hypoglycemia.

Six months after each yearly visit, a Pediatric Endocrinologist examined the patient. At this visit the patient was screened for the potential effects of treatment, and anthropometric measurements of height and weight were done by the same clinician using standardized equipment. Study drug medication records were also reviewed.

Sample Analysis

Laboratory tests were conducted for serum IGF-1 and GH levels and for CBC, platelet count, serum chemistry and thyroid function tests.

Data Analysis

The growth rate before treatment for these children is approximately 2-4.0 cm/yr. Adverse events were addressed and summarized.

Patients were discontinued from the protocol for the following reasons:

Medical conditions that required study discontinuation.

Intercurrent illness, which would, in the judgment of the Investigator, tend to affect assessments of clinical and mental status to a significant degree.

Patient, parent, or guardian desire to discontinue participation.

Non-compliance with the protocol.

Results and Discussion

In these pediatric patients who were IGFD, treatment with rhIGF-1 caused a significant increase in growth rate.

The five patients shown below in Table 2 were treated with rhIGF-1 for at least one year by twice daily subcutaneous injection of between 80 and 120 micrograms per kilogram.

TABLE 2

Patient Characteristics and Growth Rate in IGFD Patients treated with rhIGF-1

| Age (years) | GH Stimulation Test (ng · ml) | IGF-1 (ng/ml) | Ht SDS | Growth Rates (cm/year) | |
|---|---|---|---|---|---|
| | | | | Baseline | Year 1 |
| 2.4 | 22 | 25 | −3.2 | 4.2 | 8.7 |
| 3.4 | 94.3 | 47 | −4.4 | 1.5 | 9.2 |
| 4.1 | 225 | 25 | −4.5 | 3.0 | 9.4 |
| 7.8 | 83 | 115 | −2.8 | 5.1 | 8.2 |
| 8.6 | 89 | 77 | −4.9 | 3.3 | 9.5 |
| | | | Mean = | 3.6 | 9.0 |

GH Levels

The growth hormone levels measured in these patients after the GH stimulation test were all above the level designated as normal (10 ng/ml). Therefore, all the patients in the study were GH sufficient.

IGF-1 Levels

The levels of IGF-1 were compared with the normative data sets from 2 sources to estimate the IGF-1 SDS values in the 5 patients above. The IGF-1 SDS values were within the normal range (an SDS value less than 2 below the normal mean) for the above patients using at least one of the 2 normative data. These patients therefore can be designated as having Pediatric primary IGFD or severe Pediatric IGFD, depending for some patients which of the normative datasets are used to calculated the IGF-1 SDS values.

Growth Rates

The baseline height SDS score in these patients were all less than 2 below the mean. Therefore, these patients can also be designated as suffering from IGFD or severe IGFD. The baseline growth rate of the patients averaged 3.6 cm per year. When the patients were treated with rhIGF-1 their growth rates were increased to on average 9.0 cm per year. The increase in growth rate of 5.4 cm is a clinically significant increase.

The data therefore shows that treatment with rhIGF-1 in Pediatric primary IGFD patients and severe Pediatric primary IGFD patients accelerates growth rates.

All references cited herein are specifically incorporated by reference as if fully set forth herein.

Having hereinabove disclosed exemplary embodiments of the present invention, those skilled in the art will recognize that this disclosure is only exemplary such that various alternatives, adaptations, and modifications are within the scope of the invention, and are contemplated by the Applicant. Accordingly, the present invention is not limited to the specific embodiments as illustrated above, but is defined by the following claims.

What is claimed:

1. A method for treating a human pediatric subject having insulin-like growth factor-1 deficiency (IGFD) comprising;
    administering to a human pediatric subject an effective amount of insulin like growth factor-1 (IGF-1), wherein the subject is characterized as follows:
        at the time of treatment or prior to initial treatment with IGF-1, has or had a height at least about 2 standard deviations (SD) below the normal mean height for a human pediatric subject of the same age and gender,
        at the time of treatment or prior to initial treatment with IGF-1, has or had a blood level of IGF-1 at least about −1 SD below normal mean levels for a human pediatric subject of the same age and gender, and
        the human pediatric subject does not have Laron syndrome or partial growth hormone insensitivity syndrome,
    wherein said administering is effective to treat IGFD in the human pediatric subject.

2. The method of claim 1, wherein the subject is further characterized as having a blood level of growth hormone binding protein (GHBP) which is at least normal for a subject of the same age and gender.

3. The method of claim 1, wherein the subject is further characterized as having a blood level of growth hormone (GH) which is at least normal.

4. The method of claim 1, wherein said administering alleviates at least one symptom of IGFD.

5. The method of claim 1, wherein said administering provides for an increase in growth rate or height.

6. The method of claim 1, wherein the subject has a blood level of IGF-1 that is at least about 2.0 SD below normal mean levels for a subject of the same age and gender.

7. The method of claim 1, wherein IGF-1 is administered in a dose of about 20 to 240 μg/kg/day.

8. The method of claim 7, wherein said IGF-1 is administered subcutaneously.

9. A method for treating a human adult subject having insulin-like growth factor-1 deficiency (IGFD) comprising;
    administering to a human adult subject an effective amount of insulin like growth factor-1 (IGF-1), wherein the subject is characterized as follows:
        at the time of treatment or prior to initial treatment with IGF-1, has or had a height at least about 2 standard deviations (SD) below a normal mean for a human adult subject of the same age and gender,
        at the time of treatment or prior to initial treatment with IGF-1, has or had a blood level of IGF-1 at least about −1 SD below normal mean levels for a human adult subject of the same age and gender, and
    the human adult subject does not have Laron syndrome or partial growth hormone insensitivity syndrome,
    wherein said administering provides for treatment of IGFD in the human adult subject.

10. The method of claim 9, wherein the subject is further characterized as having a blood level of growth hormone binding protein (GHBP) which is at least normal for a subject of the same age and gender.

11. The method of claim 9, wherein the subject is further characterized as having a blood level of growth hormone (GH) which is at least normal.

12. The method of claim 9, wherein said administering alleviates at least one symptom of IGFD.

13. The method of claim 9, wherein the subject has a blood level of IGF-1 that is at least about 2.0 SD below normal mean levels for a subject of the same age and gender.

14. The method of claim 9, wherein IGF-1 is administered in a dose of about 20 to 240 μg/kg/day.

15. The method of claim 14, wherein said IGF-1 is administered subcutaneously.

16. A method for achieving at least normal insulin-like growth factor-1 (IGF-1) levels for age and gender in a human subject having insulin-like growth factor-1 deficiency (IGFD), comprising
    administering an effective amount of insulin-like growth factor (IGF-1) to the human subject, wherein the human subject is characterized as follows:
        at the time of treatment or prior to initial treatment with IGF-1, has or had a height at least about 2 standard deviations (SD) below a normal mean for a human subject of the same age and gender, and
        at the time of treatment or prior to initial treatment with IGF-1, has or had a blood level of IGF-1 at least about −1 SD below normal mean levels for a human subject of the same age and gender,
    wherein the human subject does not have Laron syndrome or partial growth hormone insensitivity syndrome, and wherein said administering achieves normal blood IGF-1 levels for age and gender in the human subject.

17. The method of claim 16, wherein the subject is further characterized as having a blood level of growth hormone binding protein (GHBP) which is at least normal for a subject of the same age and gender.

18. The method of claim 16, wherein the subject is further characterized as having a blood level of growth hormone (GH) which is at least normal.

19. The method of claim 16, wherein the subject has a blood level of IGF-1 that is at least about 2.0 SD below normal mean levels for a subject of the same age and gender.

20. The method of claim 16, wherein IGF-1 is administered in a dose of about 20 to 240 μg/kg/day.

21. The method of claim 20, wherein said IGF-1 is administered subcutaneously.

22. A method for treating a human subject having a primary insulin-like growth factor-1 deficiency (IGFD) comprising;
    administering to a human subject having primary insulin-like growth factor-1 deficiency (IGFD) an effective amount of insulin like growth factor-1 (IGF-1), wherein the human subject is characterized as follows:
        at the time of treatment or prior to initial treatment with IGF-1, has or had a height at least about 2 standard deviations (SD) below a normal mean for a human subject of the same age and gender,
        at the time of treatment or prior to initial treatment with IGF-1, has or had a blood level of IGF-1 at least about −1 SD below normal mean levels for a human subject of the same age and gender, and
        has a blood level of growth hormone (GH) which is at least normal, wherein the human subject does not have Laron syndrome or partial growth hormone insensitivity syndrome, and wherein said administering provides for treatment of IGFD in the human subject.

23. The method of claim 22, wherein the subject is further characterized as having a blood level of growth hormone binding protein (GHBP) which is at least normal for a subject of the same age and gender.

24. The method of claim 22, wherein said administering alleviates at least one symptom of IGFD.

25. The method of claim 22, wherein the subject is a human pediatric subject and said administering provides for an increase in growth rate or height.

26. The method of claim 22, wherein the subject has a blood level of IGF-1 that is at least about 2.0 SD below normal mean levels for a subject of the same age and gender.

27. The method of claim 22, wherein IGF-1 is administered in a dose of about 20 to 240 µg/kg/day.

28. The method of claim 27, wherein said IGF-1 is administered subcutaneously.

29. A method for achieving at least normal insulin-like growth factor-1 (IGF-1) levels for age and gender in a human subject having primary insulin-like growth factor-1 deficiency (IGFD), comprising administering an effective amount of insulin-like growth factor (IGF-1) to a human subject, wherein the human subject is characterized as follows:

at the time of treatment or prior to initial treatment with IGF-1, has or had a height at least about 2 standard deviations (SD) below normal mean for a human subject of the same age and gender, at the time of treatment or prior to initial treatment with IGF-1, has or had a blood level of IGF-1 at least about −1 SD below normal mean levels for a human subject of the same age and gender, and has a blood level of growth hormone (GH) which is at least normal;

wherein the human subject does not have Laron syndrome or partial growth hormone insensitivity syndrome, wherein said administering achieves normal blood IGF-1 levels for age and gender in the human subject.

30. The method of claim 29, wherein the subject is further characterized as having a blood level of growth hormone binding protein (GHBP) which is at least normal for a subject of the same age and gender.

31. The method of claim 29, wherein the subject has a blood level of IGF-1 that is at least about 2.0 SD below normal mean levels for a subject of the same age and gender.

32. The method of claim 29, wherein IGF-1 is administered in a dose of about 20 to 240 µg/kg/day.

33. The method of claim 32, wherein said IGF-1 is administered subcutaneously.

* * * * *

UNITED STATES PATENT AND TRADEMARK OFFICE
CERTIFICATE OF CORRECTION

PATENT NO. : 7,258,864 B2
APPLICATION NO. : 10/939111
DATED : August 21, 2007
INVENTOR(S) : Ross G. Clark It is certified that error appears in the above-identified patent and that said Letters Patent is hereby corrected as shown below:

In column 37, line 26, the words "-1 SD" should be replaced with -- 1 SD --.

In column 37, line 62, the words "-1 SD" should be replaced with -- 1 SD --.

In column 38, line 31, the words "-1 SD" should be replaced with -- 1 SD --.

In column 38, line 64, the words "-1 SD" should be replaced with -- 1 SD --.

In column 40, line 7, the words "-1 SD" should be replaced with -- 1 SD --.

Signed and Sealed this

Tenth Day of February, 2009

JOHN DOLL
*Acting Director of the United States Patent and Trademark Office*